US009719136B2

(12) United States Patent
Betts et al.

(10) Patent No.: US 9,719,136 B2
(45) Date of Patent: Aug. 1, 2017

(54) METHODS FOR ADDING ADAPTERS TO NUCLEIC ACIDS AND COMPOSITIONS FOR PRACTICING THE SAME

(71) Applicant: Clontech Laboratories, Inc., Mountain View, CA (US)

(72) Inventors: Craig Betts, Mountain View, CA (US); Andrew Alan Farmer, Los Altos, CA (US)

(73) Assignee: Takara Bio USA, Inc., Mountain View, CA (US)

( * ) Notice: Subject to any disclaimer, the term of this patent is extended or adjusted under 35 U.S.C. 154(b) by 204 days.

(21) Appl. No.: 14/566,445

(22) Filed: Dec. 10, 2014

(65) Prior Publication Data
US 2015/0203906 A1    Jul. 23, 2015

Related U.S. Application Data

(60) Provisional application No. 61/917,101, filed on Dec. 17, 2013, provisional application No. 61/979,856, filed on Apr. 15, 2014.

(51) Int. Cl.
*C12Q 1/68* (2006.01)
*C12P 19/34* (2006.01)
*C12N 15/10* (2006.01)

(52) U.S. Cl.
CPC ....... *C12Q 1/6869* (2013.01); *C12N 15/1096* (2013.01)

(58) Field of Classification Search
None
See application file for complete search history.

(56) References Cited

U.S. PATENT DOCUMENTS

| | | | |
|---|---|---|---|
| 5,683,896 A | 11/1997 | Hartley et al. | |
| 5,962,271 A | 10/1999 | Chenchik et al. | |
| 5,962,272 A | 10/1999 | Chenchik et al. | |
| 6,251,639 B1 | 6/2001 | Kurn | |
| 6,287,823 B1 | 9/2001 | Hartley | |
| 6,406,890 B1 | 6/2002 | Mueller | |
| 6,518,026 B2 | 2/2003 | Hartley | |
| 7,435,572 B2 | 10/2008 | Bitinaite | |
| 8,124,340 B2 * | 2/2012 | Rashtchian | C12Q 1/6806 435/6.1 |
| 8,440,401 B2 | 5/2013 | Bitinaite | |
| 9,410,173 B2 * | 8/2016 | Betts | C12P 19/34 |
| 2006/0099589 A1 | 5/2006 | Pedersen et al. | |
| 2008/0009420 A1 | 1/2008 | Schroth et al. | |
| 2008/0145844 A1 | 6/2008 | Barsova et al. | |
| 2008/0182239 A1 | 7/2008 | Mullinax | |
| 2012/0010091 A1 | 1/2012 | Linnarson et al. | |
| 2012/0283106 A1 | 11/2012 | Wang et al. | |
| 2014/0242581 A1 | 8/2014 | Johnson | |
| 2015/0079600 A1 | 3/2015 | Bergmann | |

FOREIGN PATENT DOCUMENTS

| | | |
|---|---|---|
| DE | 196 01 385 A1 | 7/1997 |
| EP | 1 369 480 A1 | 12/2003 |
| KR | 2002-0036665 A | 5/2002 |
| WO | 97/24455 A2 | 7/1997 |
| WO | WO 01/09310 A1 | 2/2001 |
| WO | 02/00938 A2 | 1/2002 |
| WO | 02/068629 A2 | 9/2002 |
| WO | WO 2005/019452 A1 | 3/2005 |
| WO | 2012/042374 A2 | 4/2012 |
| WO | 2012/116146 A1 | 8/2012 |
| WO | WO2013012344 2 | 8/2013 |
| WO | 2014/066179 A1 | 5/2014 |
| WO | WO 2015/057319 A1 | 4/2015 |
| WO | WO2015005731 9 | 4/2015 |
| WO | WO 2015/173402 A1 | 11/2015 |

OTHER PUBLICATIONS

Schramm et al. "A simple and reliable 5'-RACE approach", Nucleic Acids Research, 2000, vol. 28, No. 22, e96, 4 pages.
Turchinovich et al. "Capture and Amplification by Tailing and Switching (CATS): An ultrasensitive ligation-independent method for generation of DNA libraries for deep sequencing from pictogram amounts of DNA and RNA", RNA Biology, vol. 11, No. 7, pp. 817-828 (Jul. 2014).
Hoshino, et al. "A comparative study of microbial diversity and community structure in marine sediments using poly (A) tailing and reverse transcription-PCR", Front Microbiol. 2013; 4: 160.
Picelli, et al. "Full-length RNA-seq from single cells using Smart-seq2", Nature Protocols 9,171-181(2014), Abstract Only.
Shi, et al. "Poly(T) adaptor RT-PCR", Methods Mol Biol. 2012;822:53-66. doi: 10.1007/978-1-61779-427-8_4.
Islam et al. "Highly multiplexed and strand-specific single-cell RNA 5' end sequencing", Nature Protocols 7 (2012), 813-828.
Kapteyn et al. "Incorporation of non-natural nucleotides into template-switching oligonucleotides reduces background and improves cDNA synthesis from very small RNA samples," BMC Genomics, 2010, 11: 413.
Kivioja et al. "Counting absolute numbers of molecules using unique molecular identifiers", Nature Methods 9 (2012), 72-74.
Kurzynska-Kokorniak et al. "DNA-directed DNA Polymerase and Strand Displacement Activity of the Reverse Transcriptase Encoded by the R2 Retrotransposon", Journal of Molecular Biology 374(2): 322-333 (2007).

(Continued)

*Primary Examiner* — David Thomas
(74) *Attorney, Agent, or Firm* — Otto C. Guedelhoefer, IV; Bret E. Field; Bozicevic, Field & Francis LLP

(57) ABSTRACT

Provided are methods of adding adapters to nucleic acids. The methods include combining in a reaction mixture a template nucleic acid, a template switch oligonucleotide, a polymerase, and dNTPs. The reaction mixture components are combined under conditions sufficient to produce a product nucleic acid that includes the template nucleic acid and the template switch oligonucleotide each hybridized to adjacent regions of a single product nucleic acid including a region polymerized from the dNTPs by the polymerase. The methods further include attaching sequencing platform adapter constructs to ends of the product nucleic acid or a derivative thereof. Aspects of the invention further include compositions and kits.

19 Claims, 4 Drawing Sheets

(56) References Cited

OTHER PUBLICATIONS

Levin et al. "Comprehensive comparative analysis of strand-specific RNA sequencing methods", Nature Methods 7 (2010), 709-715.
Matz et al. "Amplification of cDNA ends based on template-switching effect and step-out PCR," Nucleic Acids Research, 1999, vol. 27, No. 6, 1558-1560.
Oz-Gleenberg et al. "Reverse transcriptases can clamp together nucleic acids strands with two complementary bases at their 3'-termini for initiating DNA synthesis", Nucleic Acids Research 39(3): 1042-1053 (2010).
Oz-Gleenberg et al. "Substrate variations that affect the nucleic acid clamp activity of reverse transcriptases", FEBS Journal 279(10): 1894-1903 (2012).
Zhuang et al. "Structural bias in T4 RNA ligase-mediated 3'-adapter ligation", Nucleic Acids Research 40(7): e54 (2012), 14 pages.
Hernandez, et al. "Identification of anaplastic lymphoma kinase variant translocations using 5'RACE", Methods Mol Med. 2005;115:295-314.
Communication pursuant to Article 94(3) EPC for European patent application No. 13848994.3, mailed Feb. 15, 2017, 9 pages.

* cited by examiner

METHODS FOR ADDING ADAPTERS TO NUCLEIC ACIDS AND COMPOSITIONS FOR PRACTICING THE SAME

CROSS REFERENCE TO RELATED APPLICATIONS

Pursuant to 35 U.S.C. §119 (e), this application claims priority to the filing date of the U.S. Provisional Patent Application Ser. No. 61/917,101, filed Dec. 17, 2013 and U.S. Provisional Patent Application Ser. No. 61/979,856, filed Apr. 15, 2014; the disclosure of which applications are herein incorporated by reference.

INTRODUCTION

Massively parallel (or "next generation") sequencing platforms are rapidly transforming data collection and analysis in genome, epigenome and transcriptome research. Certain sequencing platforms, such as those marketed by Illumina®, Ion Torrent™, Roche™, and Life Technologies™, involve solid phase amplification of polynucleotides of unknown sequence. Solid phase amplification of these polynucleotides is typically performed by first ligating known adapter sequences to each end of the polynucleotide. The double-stranded polynucleotide is then denatured to form a single-stranded template molecule. The adapter sequence on the 3' end of the template is hybridized to an extension primer that is immobilized on the solid substrate, and amplification is performed by extending the immobilized primer. In what is often referred to as "bridge PCR", a second immobilized primer, identical to the 5' end of the template, serves as a reverse primer, allowing amplification of both the forward and reverse strands to proceed on the solid substrate, e.g., a bead or surface of a flow cell.

A disadvantage of ligation-based approaches for sequencing adapter addition is the number of steps involved, including the enzymatic and wash steps that are needed to prepare the target polynucleotide before solid phase amplification can be initiated. As one example, after ligation of the adapter sequences, unused adapter molecules must be separated from the ligated polynucleotides before adding the mixture to the flow cell. Otherwise, the unused adapter molecules can also hybridize to the immobilized primers, preventing efficient hybridization of the primers to the template molecules and subsequent extension.

An additional drawback of ligation-based approaches is their lack of directionality, which makes it difficult to have different adapters at the different ends of the nucleic acids. Moreover, the sensitivity of such methods is low and renders them unsuitable under circumstances where only a small amount of sample material is available.

SUMMARY

Provided are methods of adding adapters to nucleic acids. The methods include combining in a reaction mixture a template nucleic acid, a template switch oligonucleotide, a polymerase, and dNTPs. The reaction mixture components are combined under conditions sufficient to produce a product nucleic acid that includes the template nucleic acid and the template switch oligonucleotide each hybridized to adjacent regions of a single product nucleic acid including a region polymerized from the dNTPs by the polymerase. The methods further include attaching sequencing platform adapter constructs to ends of the product nucleic acid or a derivative thereof. Aspects of the invention further include compositions and kits.

DETAILED DESCRIPTION

Figure 1:
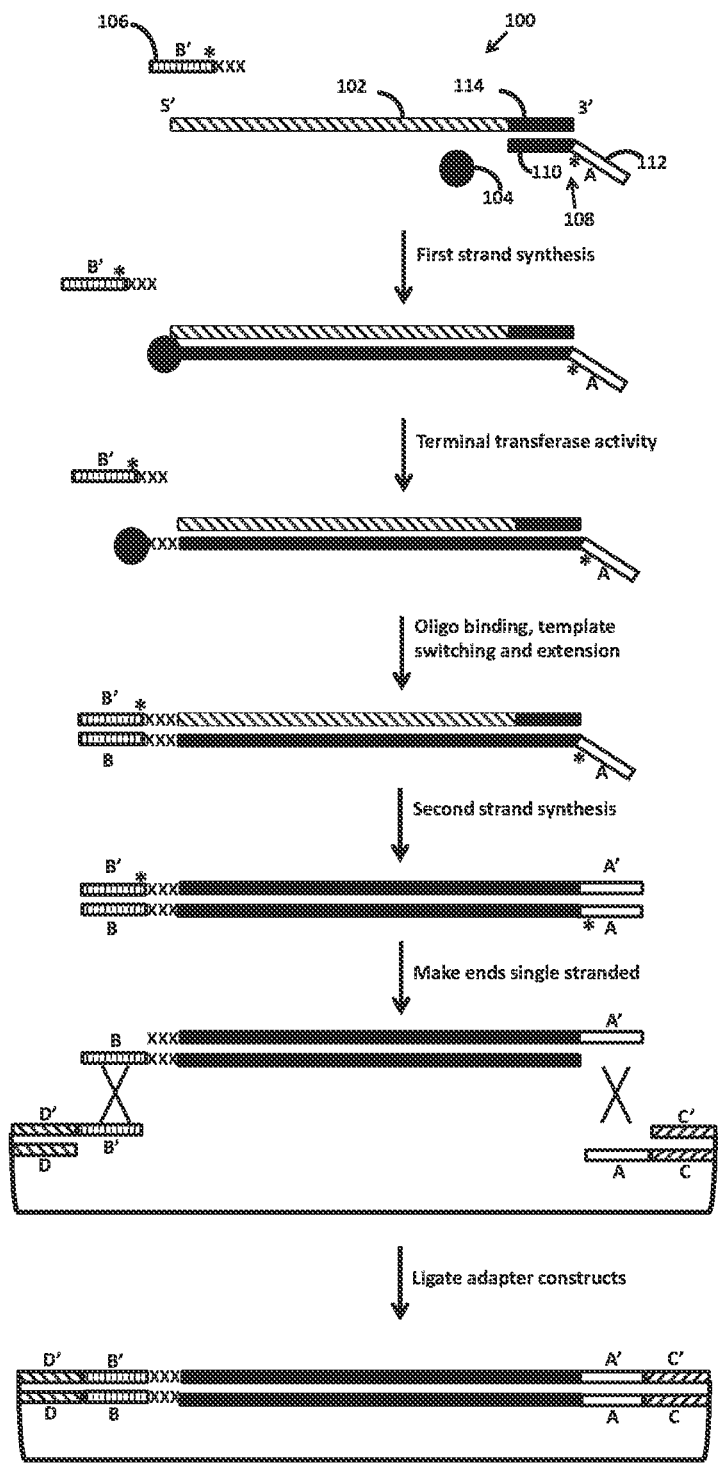
FIG. 1 schematically illustrates a template switch-based method for generating a nucleic acid having adapter constructs according to one embodiment of the present disclosure. In this embodiment, first strand synthesis is carried out using a primer and a template switch oligonucleotide, each of which include one or more exo-sample nucleotides that facilitate the generation of single-stranded overhangs to which sequencing platform adapter constructs are attached.

Provided are methods of adding adapters to nucleic acids. The methods include combining in a reaction mixture a template nucleic acid, a template switch oligonucleotide, a polymerase, and dNTPs. The reaction mixture components are combined under conditions sufficient to produce a product nucleic acid that includes the template nucleic acid and the template switch oligonucleotide each hybridized to adjacent regions of a single product nucleic acid including a region polymerized from the dNTPs by the polymerase. The methods further include attaching sequencing platform adapter constructs to ends of the product nucleic acid or a derivative thereof. Aspects of the invention further include compositions and kits.

Before the methods of the present disclosure are described in greater detail, it is to be understood that the methods are not limited to particular embodiments described, as such may, of course, vary. It is also to be understood that the terminology used herein is for the purpose of describing particular embodiments only, and is not intended to be limiting, since the scope of the methods will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the methods. The upper and lower limits of these smaller ranges may independently be included in the smaller ranges and are also encompassed within the methods, subject to any specifically excluded limit in the stated range. Where the stated range includes one or both of the limits, ranges excluding either or both of those included limits are also included in the methods.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which the methods belong. Although any methods similar or equivalent to those described herein can also be used in the practice or testing of the methods, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present methods are not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the methods, which are, for clarity, described in the context of separate embodiments, may also be provided in combination in a single embodiment. Conversely, various features of the methods, which are, for brevity, described in the context of a single embodiment, may also be provided separately or in any suitable sub-combination. All combinations of the embodiments are specifically embraced by the present invention and are disclosed herein just as if each and every combination was individually and explicitly disclosed, to the extent that such combinations embrace operable processes and/or devices/systems/kits. In addition, all sub-combinations listed in the embodiments describing such variables are also specifically embraced by the present methods and are disclosed herein just as if each and every such sub-combination was individually and explicitly disclosed herein.

As will be apparent to those of skill in the art upon reading this disclosure, each of the individual embodiments described and illustrated herein has discrete components and features which may be readily separated from or combined with the features of any of the other several embodiments without departing from the scope or spirit of the present methods. Any recited method can be carried out in the order of events recited or in any other order which is logically possible.

Methods

Methods of adding sequencing platform adapters to nucleic acids are provided. As described in greater detail below, sequencing platform adaptors are nucleic acid sequences that are present at the ends of a target nucleic acid to be sequenced and are employed in a sequencing protocol. A given sequencing platform adapter of interest may vary in length, and in some instances may range from 4 to 200 nucleotides in length. For example, the adapter may be from 4 to 100 nucleotides in length, such as from 6 to 75, from 8 to 50, or from 10 to 40 nucleotides in length. As will be described in greater detail below, embodiments of the methods may result in addition of the same sequencing platform adaptors (i.e., sequencing platform adaptors of identical sequence) to each end of the target nucleic acid. Alternatively, embodiments of the methods may result in the addition of different sequencing platform adaptors (i.e., sequence platform adaptors of different sequence) to each end of the target nucleic acid. Where desired, the sequencing platform adaptors may be added to the target nucleic acid in a directional manner, by which is meant that the end of the sequencing platform adaptor that is joined to the end of the target nucleic acid is known.

The methods utilize the ability of certain nucleic acid polymerases to "template switch," using a first nucleic acid strand as a template for polymerization, and then switching to a second template nucleic acid strand (which may be referred to as a "template switch nucleic acid" or an "acceptor template") while continuing the polymerization reaction. The result is the synthesis of a hybrid nucleic acid strand with a 5' region complementary to the first template nucleic acid strand and a 3' region complementary to the template switch nucleic acid. In certain aspects, the nucleotide sequence of all or a portion (e.g., a 5' region) of the template switch oligonucleotide may be defined by a practitioner of the subject methods such that the newly-synthesized hybrid nucleic acid strand has a partial or complete sequencing platform adapter sequence at its 3' end useful for sequencing the hybrid nucleic acid strand using a sequencing platform of interest. Sequencing platforms of interest include, but are not limited to, the HiSeq™, MiSeq™ and Genome Analyzer™ sequencing systems from Illumina®; the Ion PGM™ and Ion Proton™ sequencing systems from Ion Torrent™; the PACBIO RS II sequencing system from Pacific Biosciences, the SOLiD sequencing systems from Life Technologies™, the 454 GS FLX+ and GS Junior sequencing systems from Roche, or any other sequencing platform of interest.

In certain aspects, the polymerization reaction is initiated using a primer having a partial or complete sequencing platform adapter sequence at its 5' end, resulting in a hybrid nucleic acid strand having a partial or complete sequencing platform adapter sequence at each end. The directionality of the adapters in the hybrid nucleic acid strand may be predetermined by a practitioner of the subject methods, e.g., by selecting the adapter sequence present at the 5' end of the primer, and the adapter sequence present at the 5' end of the template switch oligonucleotide. Here, the adapter sequence present in the primer and the adapter sequence in the template switch oligonucleotide will be present at the 5' and 3' ends of the hybrid nucleic acid strand, respectively.

According to the methods of the present disclosure, the reaction mixture components are combined under conditions sufficient to produce a product nucleic acid that includes the template nucleic acid and the template switch oligonucleotide each hybridized to adjacent regions of a single product nucleic acid that includes a region polymerized from the dNTPs by the polymerase.

By "conditions sufficient to produce a product nucleic acid" is meant reaction conditions that permit polymerase-mediated extension of a 3' end of a nucleic acid strand hybridized to the template nucleic acid, template switching of the polymerase to the template switch oligonucleotide, and continuation of the extension reaction using the template switch oligonucleotide as the template. Achieving suitable reaction conditions may include selecting reaction mixture components, concentrations thereof, and a reaction temperature to create an environment in which the polymerase is active and the relevant nucleic acids in the reaction interact (e.g., hybridize) with one another in the desired manner. For example, in addition to the template nucleic acid, the polymerase, the template switch oligonucleotide and dNTPs, the reaction mixture may include buffer components that establish an appropriate pH, salt concentration (e.g., KCl concentration), metal cofactor concentration (e.g., $Mg^{2+}$ or $Mn^{2+}$ concentration), and the like, for the extension reaction and template switching to occur. Other components may be included, such as one or more nuclease inhibitors (e.g., an RNase inhibitor and/or a DNase inhibitor), one or more additives for facilitating amplification/replication of GC rich sequences (e.g., GC-Melt™ reagent (Clontech Laboratories, Inc. (Mountain View, Calif.)), betaine, single-stranded binding proteins (e.g., T4 Gene 32, cold shock protein A (CspA), and/or the like) DMSO, ethylene glycol, 1,2-propanediol, or combinations thereof), one or more molecular crowding agents (e.g., polyethylene glycol, or the like), one or more enzyme-stabilizing components (e.g., DTT present at a final concentration ranging from 1 to 10 mM (e.g., 5 mM)), and/or any other reaction mixture components useful for facilitating polymerase-mediated extension reactions and template-switching. In certain aspects, when the template nucleic acid is RNA, and when the extension reaction has proceeded for a desired amount of time, RNase H is added to hydrolyze any template RNAs that hybridized to the nascent cDNA strands.

The reaction mixture can have a pH suitable for the primer extension reaction and template-switching. In certain embodiments, the pH of the reaction mixture ranges from 5 to 9, such as from 7 to 9, including from 8 to 9, e.g., 8 to 8.5. In some instances, the reaction mixture includes a pH adjusting agent. pH adjusting agents of interest include, but are not limited to, sodium hydroxide, hydrochloric acid, phosphoric acid buffer solution, citric acid buffer solution, and the like. For example, the pH of the reaction mixture can be adjusted to the desired range by adding an appropriate amount of the pH adjusting agent.

The temperature range suitable for production of the product nucleic acid may vary according to factors such as the particular polymerase employed, the melting temperatures of any optional primers employed, etc. According to one embodiment, the polymerase is a reverse transcriptase (e.g., an MMLV reverse transcriptase) and the reaction mixture conditions sufficient to produce the product nucleic acid include bringing the reaction mixture to a temperature ranging from 4° C. to 72° C., such as from 16° C. to 70° C., e.g., 37° C. to 50° C., such as 40° C. to 45° C., including 42° C.

The template nucleic acid (e.g., a template DNA, a template RNA, or the like) may be a polymer of any length composed of deoxyribonucleotides, ribonucleotides, or combinations thereof, e.g., 10 bases or longer, 20 bases or longer, 50 bases or longer, 100 bases or longer, 500 bases or longer, 1000 bases or longer, 2000 bases or longer, 3000 bases or longer, 4000 bases or longer, 5000 bases or longer or more bases. In certain aspects, the template nucleic acid is a polymer composed of deoxyribonucleotides or ribonucleotides, e.g., 10 bases or less, 20 bases or less, 50 bases or less, 100 bases or less, 500 bases or less, 1000 bases or less, 2000 bases or less, 3000 bases or less, 4000 bases or less, or 5000 bases or less.

In certain aspects, the template nucleic acid is a template deoxyribonucleic acid (template DNA). Template DNAs of interest include, but are not limited to, genomic DNA or fragments thereof, complementary DNA (or "cDNA", synthesized from any RNA or DNA of interest), recombinant DNA (e.g., plasmid DNA), or the like.

According to certain embodiments, the template nucleic acid is a template ribonucleic acid (template RNA). The template RNA may be any type of RNA (or sub-type thereof) including, but not limited to, a messenger RNA (mRNA), a microRNA (miRNA), a small interfering RNA (sRNA), a transacting small interfering RNA (ta-sRNA), a natural small interfering RNA (nat-sRNA), a ribosomal RNA (rRNA), a transfer RNA (tRNA), a small nucleolar RNA (snoRNA), a small nuclear RNA (snRNA), a long non-coding RNA (lncRNA), a non-coding RNA (ncRNA), a transfer-messenger RNA (tmRNA), a precursor messenger RNA (pre-mRNA), a small Cajal body-specific RNA (scaRNA), a piwi-interacting RNA (piRNA), an endoribonuclease-prepared sRNA (esiRNA), a small temporal RNA (stRNA), a signal recognition RNA, a telomere RNA, a ribozyme, or any combination of RNA types thereof or subtypes thereof.

The nucleic acid sample that includes the template nucleic acid may be combined into the reaction mixture in an amount sufficient for producing the product nucleic acid. According to one embodiment, the nucleic acid sample is combined into the reaction mixture such that the final concentration of nucleic acid in the reaction mixture is from 1 μg/μL to 10 μg/μL, such as from 1 μg/μL to 5 μg/μL, such as from 0.001 μg/μL to 2.5 μg/μL, such as from 0.005 μg/μL to 1 μg/μL, such as from 0.01 μg/μL to 0.5 μg/μL, including from 0.1 μg/μL to 0.25 μg/μL. In certain aspects, the nucleic acid sample that includes the template nucleic acid is isolated from a single cell. In other aspects, the nucleic acid sample that includes the template nucleic acid is isolated from 2, 3, 4, 5, 6, 7, 8, 9, 10 or more, 20 or more, 50 or more, 100 or more, or 500 or more cells. According to certain embodiments, the nucleic acid sample that includes the template nucleic acid is isolated from 500 or less, 100 or less, 50 or less, 20 or less, 10 or less, 9, 8, 7, 6, 5, 4, 3, or 2 cells.

The template nucleic acid may be present in any nucleic acid sample of interest, including but not limited to, a nucleic acid sample isolated from a single cell, a plurality of cells (e.g., cultured cells), a tissue, an organ, or an organism (e.g., bacteria, yeast, or the like). In certain aspects, the nucleic acid sample is isolated from a cell(s), tissue, organ, and/or the like of a mammal (e.g., a human, a rodent (e.g., a mouse), or any other mammal of interest). In other aspects, the nucleic acid sample is isolated from a source other than a mammal, such as bacteria, yeast, insects (e.g., *drosophila*), amphibians (e.g., frogs (e.g., *Xenopus*)), viruses, plants, or any other non-mammalian nucleic acid sample source.

Approaches, reagents and kits for isolating nucleic acids from such sources are known in the art. For example, kits for isolating nucleic acids from a source of interest—such as the NucleoSpin®, NucleoMag® and NucleoBond® genomic DNA or RNA isolation kits by Clontech Laboratories, Inc. (Mountain View, Calif.)—are commercially available. In certain aspects, the nucleic acid is isolated from a fixed biological sample, e.g., formalin-fixed, paraffin-embedded (FFPE) tissue. Nucleic acids from FFPE tissue may be isolated using commercially available kits—such as the NucleoSpin® FFPE DNA or RNA isolation kits by Clontech Laboratories, Inc. (Mountain View, Calif.).

In certain aspects, the subject methods include producing the template nucleic acid from a precursor nucleic acid. For example, when it is desirable to control the size of the template nucleic acid that is combined into the reaction mixture, a nucleic acid sample isolated from a source of interest may be subjected to shearing/fragmentation, e.g., to generate a template nucleic acid that is shorter in length as compared to a precursor non-sheared nucleic acid (e.g., genomic DNA, full-length mRNA, and/or the like) in the original sample. The template nucleic acid may be generated by a shearing/fragmentation strategy including, but not limited to, passing the sample one or more times through a micropipette tip or fine-gauge needle, nebulizing the sample, sonicating the sample (e.g., using a focused-ultrasonicator by Covaris, Inc. (Woburn, Mass.)), bead-mediated shearing, enzymatic shearing (e.g., using one or more DNA- or RNA-shearing enzymes), chemical based fragmentation, e.g., using divalent cations (e.g., $Mg^{2+}$, $Mn^{2+}$, and/or $Zn^{2+}$), fragmentation buffer (e.g., a high pH buffer), and/or heat, or any other suitable approach for shearing/fragmenting a precursor nucleic acid to generate a shorter template nucleic acid. In certain aspects, the template nucleic acid generated by shearing/fragmentation of a starting nucleic acid sample has a length of from 50 to 10,000 nucleotides, from 100 to 5000 nucleotides, from 150 to 2500 nucleotides, from 200 to 1000 nucleotides, e.g., from 250 to 500 nucleotides in length, for example.

In certain aspects, when the template nucleic acid is a template DNA, the subject methods include producing the template DNA from a precursor DNA (e.g., a precursor double-stranded DNA (dsDNA) or precursor single-stranded DNA (ssDNA)). For example, if a precursor dsDNA has an overhang at one or both of its ends, it may be desirable to process the precursor DNA to generate a template dsDNA having blunt ends. Approaches for generating dsDNA with blunt ends are known in the art. For example, the large (Klenow) fragment of DNA polymerase I may be used to fill in 5' overhangs, while T4 DNA polymerase may be used to trim 3' overhangs.

In other aspects, a precursor dsDNA may have blunt ends and it may be desirable to generate and employ a template DNA having an overhang (e.g., a 3' overhang) at one or both of its ends. By "overhang" is meant one or more unpaired nucleotides at an end of an otherwise double-stranded DNA molecule. These overhangs may be useful, e.g., to provide a template-primer substrate for the polymerase. That is, when the template DNA has an overhang at one of its ends, the strand that is longer at that end can serve as the DNA template, while the strand that is shorter at that end can effectively serve as a primer for initiating a nucleic acid polymerization reaction. Accordingly, the addition of a primer to the reaction mixture is not necessary when the template DNA has an overhang at one (or both) of its ends, as a first strand synthesis reaction can occur by virtue of the overhang providing a template-primer substrate for the polymerase.

Strategies for generating DNA having overhangs are known and may include contacting/digesting a precursor dsDNA (e.g., a genomic DNA, a cDNA, or the like) with a restriction endonuclease, thereby producing a template DNA having an overhang (or "sticky end") at one or both ends of the template DNA. Restriction endonucleases and the types of overhangs generated thereby are well characterized and can be selected by one practicing the subject methods to produce a template DNA having a desired type of overhang.

Alternatively, or additionally, when the template nucleic is a template DNA, a DNA "tailing" reaction may be performed to generate the template DNA having a desired overhang. According to one embodiment, the subject methods include contacting a precursor DNA with a terminal transferase in the presence of one or more types of dNTPs under conditions sufficient to produce the DNA template having the desired overhang. The rate of addition of dNTPs—and thus the length of the overhang—is a function of the ratio of 3' DNA ends to the dNTP concentration, and also which dNTP is used. The terminal transferase reaction is carried out at a temperature at which the terminal transferase is active, such as between 30° C. and 50° C., including 37° C. The dNTPs in the terminal transferase reaction may be present at a final concentration of from 0.01 mM to 1 mM (each, if more than one of the four types of dNTPs is used), such as from 0.05 mM to 0.5 mm, including 0.1 mM. The precursor DNA may be present in the terminal transferase reaction in an amount of from 0.05 to 500 pmol, such as from 0.5 to 50 pmol, including 1 to 25 pmol, e.g., 5 pmol. According to certain embodiments, the concentration of the precursor DNA in the terminal transferase reaction is from 1 attomolar (aM) to 1 nanomolar (nM), such as from 1 aM to 1 picomolar (pM), e.g., from 1 aM to 1 femtomolar (fM). A terminal transferase buffer solution and any other useful components (e.g., a metal cofactor such as Co, or the like) may also be included in the terminal transferase reaction. The terminal transferase reaction results in the addition of nucleotides at the 3' end of one or both strands of the precursor dsDNA to generate a template DNA having one or two 3' overhangs. The resulting template DNA may then be combined into the reaction mixture for generating the product nucleic acid according to the subject methods.

Additional strategies for producing the template nucleic acid from a precursor nucleic acid may be employed. For example, producing a template RNA may include adding nucleotides to an end of a precursor RNA. In certain aspects, the precursor RNA is a non-polyadenylated RNA (e.g., a microRNA, small RNA, or the like), and producing the template RNA includes adenylating (e.g., polyadenylating) the precursor RNA. Adenylating the precursor RNA may be performed using any convenient approach. According to certain embodiments, the adenylation is performed enzymatically, e.g., using Poly(A) polymerase or any other enzyme suitable for catalyzing the incorporation of adenine residues at the 3' terminus of the precursor RNA. Reaction mixtures for carrying out the adenylation reaction may include any useful components, including but not limited to, a polymerase, a buffer (e.g., a Tris-HCL buffer), one or more metal cations (e.g., $MgCl_2$, $MnCl_2$, or combinations thereof), a salt (e.g., NaCl), one or more enzyme-stabilizing components (e.g., DTT), ATP, and any other reaction components useful for facilitating the adenylation of a precursor RNA. The adenylation reaction may be carried out at a temperature (e.g., 30° C.-50° C., such as 37° C.) and pH (e.g., pH 7-pH 8.5, such as pH 7.9) compatible with the polymerase being employed, e.g., polyA polymerase. Other approaches for adding nucleotides to a precursor RNA include ligation-based strategies, where an RNA ligase (e.g., T4 RNA ligase) catalyzes the covalent joining of a defined sequence to an end (e.g., the 3' end) of the precursor RNA to produce the template RNA.

The methods of the present disclosure include combining a polymerase into the reaction mixture. A variety of polymerases may be employed when practicing the subject methods. The polymerase combined into the reaction mixture is capable of template switching, where the polymerase uses a first nucleic acid strand (e.g., a template DNA or template RNA) as a template for polymerization, and then switches to the 3' end of a second "acceptor" template nucleic acid strand (e.g., a template switch oligonucleotide) to continue the same polymerization reaction. In certain aspects, the polymerase combined into the reaction mixture is a reverse transcriptase (RT). Reverse transcriptases capable of template-switching that find use in practicing the methods include, but are not limited to, retroviral reverse transcriptase, retrotransposon reverse transcriptase, retroplasmid reverse transcriptases, retron reverse transcriptases, bacterial reverse transcriptases, group II intron-derived reverse transcriptase, and mutants, variants derivatives, or functional fragments thereof. For example, the reverse transcriptase may be a Moloney Murine Leukemia Virus reverse transcriptase (MMLV RT) or a *Bombyx mori* reverse transcriptase (e.g., *Bombyx mori* R2 non-LTR element reverse transcriptase). Polymerases capable of template switching that find use in practicing the subject methods are commercially available and include SMARTScribe™ reverse transcriptase and PrimeScript™ reverse transcriptase available from Clontech Laboratories, Inc. (Mountain View, Calif.). In certain aspects, a mix of two or more different polymerases is added to the reaction mixture, e.g., for improved processivity, proof-reading, and/or the like.

The polymerase is combined into the reaction mixture such that the final concentration of the polymerase is sufficient to produce a desired amount of the product nucleic acid. In certain aspects, the polymerase (e.g., a reverse transcriptase such as an MMLV RT or a *Bombyx mori* RT) is present in the reaction mixture at a final concentration of from 0.1 to 200 units/µL (U/µL), such as from 0.5 to 100 U/µL, such as from 1 to 50 U/µL, including from 5 to 25 U/µL, e.g., 20 U/µL.

In addition to a template switching capability, the polymerase combined into the reaction mixture may include other useful functionalities to facilitate production of the product nucleic acid. For example, the polymerase may have terminal transferase activity, where the polymerase is capable of catalyzing template-independent addition of deoxyribonucleotides to the 3' hydroxyl terminus of a DNA molecule. In certain aspects, when the polymerase reaches the 5' end of the template nucleic acid, the polymerase is capable of incorporating one or more additional nucleotides at the 3' end of the nascent strand not encoded by the template. For example, when the polymerase has terminal transferase activity, the polymerase may be capable of incorporating 1, 2, 3, 4, 5, 6, 7, 8, 9, 10 or more additional nucleotides at the 3' end of the nascent DNA strand. In certain aspects, the polymerase having terminal transferase activity incorporates 10 or less, such as 5 or less (e.g., 3) additional nucleotides at the 3' end of the nascent DNA strand. All of the nucleotides may be the same (e.g., creating a homonucleotide stretch at the 3' end of the nascent strand) or at least one of the nucleotides may be different from the other(s). In certain aspects, the terminal transferase activity of the polymerase results in the addition of a homonucleotide stretch of 2, 3, 4, 5, 6, 7, 8, 9, 10 or more of the same nucleotides (e.g., all dCTP, all dGTP, all dATP, or all dTTP). According to certain embodiments, the terminal transferase activity of the polymerase results in the addition of a homonucleotide stretch of 10 or less, such as 9, 8, 7, 6, 5, 4, 3, or 2 (e.g., 3) of the same nucleotides. For example, according to one embodiment, the polymerase is an MMLV reverse transcriptase (MMLV RT). MMLV RT incorporates additional nucleotides (predominantly dCTP, e.g., three dCTPs) at the 3' end of the nascent DNA strand. As described in greater detail elsewhere herein, these additional nucleotides may be useful for enabling hybridization between the 3' end of the template switch oligonucleotide and the 3' end of the nascent DNA strand, e.g., to facilitate template switching by the polymerase from the template nucleic acid to the template switch oligonucleotide.

As set forth above, the subject methods include combining a template switch oligonucleotide into the reaction mixture. By "template switch oligonucleotide" is meant an oligonucleotide template to which a polymerase switches from an initial template (e.g., the template nucleic acid in the subject methods) during a nucleic acid polymerization reaction. In this regard, the template nucleic acid may be referred to as a "donor template" and the template switch oligonucleotide may be referred to as an "acceptor template." As used herein, an "oligonucleotide" is a single-stranded multimer of nucleotides from 2 to 500 nucleotides, e.g., 2 to 200 nucleotides. Oligonucleotides may be synthetic or may be made enzymatically, and, in some embodiments, are 5 to 50 nucleotides in length (e.g., 9 to 50 nucleotides in length). Oligonucleotides may contain ribonucleotide monomers (i.e., may be oligoribonucleotides or "RNA oligonucleotides") or deoxyribonucleotide monomers (i.e., may be oligodeoxyribonucleotides or "DNA oligonucleotides"). Oligonucleotides may be 5 to 9, 10 to 20, 21 to 30, 31 to 40, 41 to 50, 51 to 60, 61 to 70, 71 to 80, 80 to 100, 100 to 150 or 150 to 200, up to 500 or more nucleotides in length, for example.

The reaction mixture includes the template switch oligonucleotide at a concentration sufficient to permit template switching of the polymerase from the template nucleic acid to the template switch oligonucleotide. For example, the template switch oligonucleotide may be added to the reaction mixture at a final concentration of from 0.01 to 100 µM, such as from 0.1 to 10 µM, such as from 0.5 to 5 µM, including 1 to 2 ρM (e.g., 1.2 µM).

The template switch oligonucleotide may include one or more nucleotides (or analogs thereof) that are modified or otherwise non-naturally occurring. For example, the template switch oligonucleotide may include one or more nucleotide analogs (e.g., LNA, FANA, 2'-O-Me RNA, 2'-fluoro RNA, or the like), linkage modifications (e.g., phosphorothioates, 3'-3' and 5'-5' reversed linkages), 5' and/or 3' end modifications (e.g., 5' and/or 3' amino, biotin, DIG, phosphate, thiol, dyes, quenchers, etc.), one or more fluorescently labeled nucleotides, one or more dUTP (deoxyuridine triphosphate) nucleotides, or any other feature that provides a desired functionality to the template switch oligonucleotide.

In certain aspects, the template switch oligonucleotide includes a 3' hybridization domain. The 3' hybridization domain may vary in length, and in some instances ranges from 2 to 10 nts in length, such as 3 to 7 nts in length. The sequence of the 3' hybridization may be any convenient sequence, e.g., an arbitrary sequence, a heteropolymeric sequence (e.g., a hetero-trinucleotide) or homopolymeric sequence (e.g., a homo-trinucleotide, such as G-G-G), or the like. Examples of 3' hybridization domains and template switch oligonucleotides are further described in U.S. Pat. No. 5,962,272, the disclosure of which is herein incorporated by reference.

In certain aspects, the template switch oligonucleotide includes a sequencing platform adapter construct (e.g., 5' of a 3' hybridization domain). By "sequencing platform adapter construct" is meant a nucleic acid construct that includes at least a portion of a nucleic acid domain (e.g., a sequencing platform adapter nucleic acid sequence) or complement thereof utilized by a sequencing platform of interest, such as a sequencing platform provided by Illumina® (e.g., the HiSeq™, MiSeq™ and/or Genome Analyzer™ sequencing systems); Ion Torrent™ (e.g., the Ion PGM™ and/or Ion Proton™ sequencing systems); Pacific Biosciences (e.g., the PACBIO RS II sequencing system); Life Technologies™ (e.g., a SOLiD sequencing system); Roche (e.g., the 454 GS FLX+ and/or GS Junior sequencing systems); or any other sequencing platform of interest.

In certain aspects, the template switch oligonucleotide includes a sequencing platform adapter construct that includes a nucleic acid domain selected from: a domain (e.g., a "capture site" or "capture sequence") that specifically binds to a surface-attached sequencing platform oligonucleotide (e.g., the P5 or P7 oligonucleotides attached to the surface of a flow cell in an Illumina® sequencing system); a sequencing primer binding domain (e.g., a domain to which the Read 1 or Read 2 primers of the Illumina® platform may bind); a barcode domain (e.g., a domain that uniquely identifies the sample source of the nucleic acid being sequenced to enable sample multiplexing by marking every molecule from a given sample with a specific barcode or "tag"); a barcode sequencing primer binding domain (a domain to which a primer used for sequencing a barcode binds); a molecular identification domain (e.g., a molecular index tag, such as a randomized tag of 4, 6, or other number of nucleotides) for uniquely marking molecules of interest to determine expression levels based on the number of instances a unique tag is sequenced; a complement of any such domains; or any combination thereof. In certain aspects, a barcode domain (e.g., sample index tag) and a molecular identification domain (e.g., a molecular index tag) may be included in the same nucleic acid.

The sequencing platform adapter constructs may include nucleic acid domains (e.g., "sequencing adapters") of any length and sequence suitable for the sequencing platform of interest. In certain aspects, the nucleic acid domains are from 4 to 200 nucleotides in length. For example, the nucleic acid domains may be from 4 to 100 nucleotides in length, such as from 6 to 75, from 8 to 50, or from 10 to 40 nucleotides in length. According to certain embodiments, the sequencing platform adapter construct includes a nucleic acid domain that is from 2 to 8 nucleotides in length, such as from 9 to 15, from 16-22, from 23-29, or from 30-36 nucleotides in length.

The nucleic acid domains may have a length and sequence that enables a polynucleotide (e.q., an oligonucleotide) employed by the sequencing platform of interest to specifically bind to the nucleic acid domain, e.q., for solid phase amplification and/or sequencing by synthesis of the cDNA insert flanked by the nucleic acid domains. Example nucleic acid domains include the P5 (5'-AATGATACGGCGAC-CACCGA-3')(SEQ ID NO:6), P7(5'-CAAGCA-GAAGACGGCATACGAGAT-3')(SEQ ID NO:01), Read 1 primer (5'-ACACTCTTTCCCTACACGACGCTCTTC-CGATCT-3') (SEQ ID NO:02) and Read 2 primer (5'-GTGACTGGAGTTCAGACGTGTGCTCTTCCGATCT-3') (SEQ ID NO:03) domains employed on the Illumina®-based sequencing platforms. Other example nucleic acid domains include the A adapter (5'-CCATCTCATCCCT-GCGTGTCTCCGACTCAG-3')(SEQ ID NO:04) and P1 adapter (5'-CCTCTCTATGGGCAGTCGGTGAT-3')(SEQ ID NO:05) domains employed on the Ion Torrent™-based sequencing platforms.

The nucleotide sequences of nucleic acid domains useful for sequencing on a sequencing platform of interest may vary and/or change over time. Adapter sequences are typically provided by the manufacturer of the sequencing platform (e.g., in technical documents provided with the sequencing system and/or available on the manufacturer's website). Based on such information, the sequence of the sequencing platform adapter construct of the template switch oligonucleotide (and optionally, a first strand synthesis primer, amplification primers, and/or the like) may be designed to include all or a portion of one or more nucleic acid domains in a configuration that enables sequencing the nucleic acid insert (corresponding to the template nucleic acid) on the platform of interest.

According to certain embodiments, the template switch oligonucleotide includes a modification that prevents the polymerase from switching from the template switch oligonucleotide to a different template nucleic acid after synthesizing the compliment of the 5' end of the template switch oligonucleotide (e.g., a 5' adapter sequence of the template switch oligonucleotide). Useful modifications include, but are not limited to, an abasic lesion (e.g., a tetrahydrofuran derivative), a nucleotide adduct, an iso-nucleotide base (e.g., isocytosine, isoguanine, and/or the like), or any combination thereof.

The template switch oligonucleotide may include a sequence (e.g., a defined nucleotide sequence 5' of the 3' hybridization domain of the template switch oligonucleotide), that enables second strand synthesis and/or PCR amplification of the single product nucleic acid. For example, the template switch oligonucleotide may include a sequence, where subsequent to generating the single product nucleic acid, second strand synthesis is performed using a primer that has that sequence. The second strand synthesis produces a second strand DNA complementary to the single product nucleic acid. Alternatively, or additionally, the single product nucleic acid may be amplified using a primer pair in which one of the primers has that sequence. Accordingly, in certain aspects, the methods of the present disclosure may further include producing the product nucleic acid and contacting a 3' region of the single product nucleic acid complementary to the template switch oligonucleotide with a second strand primer configured to bind thereto under hybridization conditions. Following contacting the 3' region of the single product nucleic acid complementary to the template switch oligonucleotide with the second strand primer, the methods may further include subjecting the reaction mixture to nucleic acid polymerization conditions.

The term "complementary" as used herein refers to a nucleotide sequence that base-pairs by non-covalent bonds to all or a region of a target nucleic acid (e.g., a region of the template nucleic acid, a region of the product nucleic acid, or the like). In the canonical Watson-Crick base pairing, adenine (A) forms a base pair with thymine (T), as does guanine (G) with cytosine (C) in DNA. In RNA, thymine is replaced by uracil (U). As such, A is complementary to T and G is complementary to C. In RNA, A is complementary to U and vice versa. Typically, "complementary" refers to a nucleotide sequence that is at least partially complementary. The term "complementary" may also encompass duplexes that are fully complementary such that every nucleotide in one strand is complementary to every nucleotide in the other strand in corresponding positions. In certain cases, a nucleotide sequence may be partially complementary to a target, in which not all nucleotides are complementary to every nucleotide in the target nucleic acid in all the corresponding positions. For example, a primer may be perfectly (i.e., 100%) complementary to the target nucleic acid, or the primer and the target nucleic acid may share some degree of complementarity which is less than perfect (e.g., 70%, 75%, 85%, 90%, 95%, 99%). The percent identity of two nucleotide sequences can be determined by aligning the sequences for optimal comparison purposes (e.g., gaps can be introduced in the sequence of a first sequence for optimal alignment). The nucleotides at corresponding positions are then compared, and the percent identity between the two sequences is a function of the number of identical positions shared by the sequences (i.e., % identity=# of identical positions/total # of positions×100). When a position in one sequence is occupied by the same nucleotide as the corresponding position in the other sequence, then the molecules are identical at that position. A non-limiting example of such a mathematical algorithm is described in Karlin et al., Proc. Natl. Acad. Sci. USA 90:5873-5877 (1993). Such an algorithm is incorporated into the NBLAST and XBLAST programs (version 2.0) as described in Altschul et al., Nucleic Acids Res. 25:389-3402 (1997). When utilizing BLAST and Gapped BLAST programs, the default parameters of the respective programs (e.g., NBLAST) can be used. In one aspect, parameters for sequence comparison can be set at score=100, wordlength=12, or can be varied (e.g., wordlength=5 or wordlength=20).

As used herein, the term "hybridization conditions" means conditions in which a primer specifically hybridizes to a region of the target nucleic acid (e.g., the template nucleic acid, the single product nucleic acid, etc.). Whether a primer specifically hybridizes to a target nucleic acid is determined by such factors as the degree of complementarity between the polymer and the target nucleic acid and the temperature at which the hybridization occurs, which may be informed by the melting temperature ($T_M$) of the primer. The melting temperature refers to the temperature at which half of the primer-target nucleic acid duplexes remain hybridized and half of the duplexes dissociate into single strands. The $T_m$ of a duplex may be experimentally determined or predicted using the following formula $T_m=81.5+16.6(\log_{10}[Na^+])+0.41$ (fraction G+C)$-(60/N)$, where N is the chain length and $[Na^+]$ is less than 1 M. See Sambrook and Russell (2001; Molecular Cloning: A Laboratory Manual, $3^{rd}$ ed., Cold Spring Harbor Press, Cold Spring Harbor N.Y., Ch. 10). Other more advanced models that depend on various parameters may also be used to predict $T_m$ of primer/target duplexes depending on various hybridization conditions. Approaches for achieving specific nucleic acid hybridization may be found in, e.g., Tijssen, Laboratory Techniques in Biochemistry and Molecular Biology-Hybridization with Nucleic Acid Probes, part I, chapter 2, "Overview of principles of hybridization and the strategy of nucleic acid probe assays," Elsevier (1993).

As described above, the subject methods include combining dNTPs into the reaction mixture. In certain aspects, each of the four naturally-occurring dNTPs (dATP, dGTP, dCTP and dTTP) are added to the reaction mixture. For example, dATP, dGTP, dCTP and dTTP may be added to the reaction mixture such that the final concentration of each dNTP is from 0.01 to 100 mM, such as from 0.1 to 10 mM, including 0.5 to 5 mM (e.g., 1 mM). According to one embodiment, at least one type of nucleotide added to the reaction mixture is a non-naturally occurring nucleotide, e.g., a modified nucleotide having a binding or other moiety (e.g., a fluorescent moiety) attached thereto, a nucleotide analog, or any other type of non-naturally occurring nucleotide that finds use in the subject methods or a downstream application of interest.

The addition of a primer to the reaction mixture is not necessary when the template nucleic acid provides a suitable substrate for initiation of first-strand synthesis. For example, when the template DNA or RNA has double-stranded regions and an overhang at one or both of its ends, the "non-overhanging" strand of the dsDNA or dsRNA can prime a first-strand synthesis reaction in which the overhanging strand serves as the template. In this manner, the polymerase may be used to "fill in" the overhang, switch to the template switch oligonucleotide, and complete the first strand synthesis using the template switch oligonucleotide as an acceptor template to produce the product nucleic acid (where a terminal transferase reaction by the polymerase optionally precedes the template switch as described elsewhere herein). Accordingly, the addition of a primer is obviated when the template nucleic acid includes, e.g., an overhang at one or both of its ends.

In certain circumstances, however, it may be desirable to add a primer to the reaction mixture to prime the synthesis of the single product nucleic acid. For example, if the template nucleic acid is single-stranded, a primer may be useful for purposes of initiating first-strand synthesis. In addition, use of a primer can give a practitioner of the subject methods more control over which nucleic acids in a nucleic acid sample will serve as the template nucleic acids for production of the product nucleic acid, e.g., where it is desirable to produce product nucleic acids corresponding to a template nucleic acid of interest (e.g., a particular template DNA or RNA of interest, or a polyadenylated RNA, for which an oligo dT-based primer that hybridizes to the polyA tail of the RNA may be used to prime the first strand synthesis).

Accordingly, in certain aspects, the subject methods include contacting the template nucleic acid with a first primer that primes the synthesis of the single product nucleic acid. The contacting is performed under conditions sufficient for the primer to hybridize to the template nucleic acid, which conditions are described elsewhere herein. According to one embodiment, the entire sequence of the primer is arbitrary, e.g., the primer may be a random hexamer or any other random primer of suitable length (or mixtures thereof). In other aspects, the primer has a defined sequence, e.g., the primer sequence may be designed by one practicing the subject methods to specifically hybridize to a known complementary sequence in a template nucleic acid of interest (e.g., a DNA template of interest, a polyA tail of a template RNA, or the like).

According to certain embodiments, the primer includes two or more domains. For example, the primer may include a first (e.g., 3') domain that hybridizes to the template nucleic acid and a second (e.g., 5') domain that does not hybridize to the template nucleic acid. The sequence of the first and second domains may be independently defined or arbitrary. In certain aspects, the first domain has a defined sequence and the sequence of the second domain is defined or arbitrary. In other aspects, the first domain has an arbitrary sequence (e.g., a random sequence, such as a random hexamer sequence) and the sequence of the second domain is defined or arbitrary. According to one embodiment, the second domain includes a nucleotide sequence that is the same as, or different from, a nucleotide sequence present in the template switch oligonucleotide.

In some embodiments, the second domain of the primer includes a sequencing platform adapter construct. The sequencing platform adapter construct of the second domain may include a nucleic acid domain selected from a domain (e.g., a "capture site" or "capture sequence") or complement thereof that specifically binds to a surface-attached sequencing platform oligonucleotide (e.g., the P5 or P7 oligonucleotides attached to the surface of a flow cell in an Illumina® sequencing system), a sequencing primer binding domain (e.g., a domain to which the Read 1 or Read 2 primers of the Illumina® platform may bind), a barcode domain (e.g., a domain that uniquely identifies the sample source of the nucleic acid being sequenced to enable sample multiplexing by marking every molecule from a given sample with a specific barcode or "tag"), a barcode sequencing primer binding domain (a domain to which a primer used for sequencing a barcode binds), a molecular identification domain, a complement of any such domains, or any combination thereof.

In certain aspects, the sequencing platform adapter construct of the second domain of the primer is different from any sequencing platform adapter construct of the template switch oligonucleotide. Such embodiments find use, e.g., where one wishes to produce a single product nucleic acid (e.g., a cDNA or library thereof) with one end having one or more sequencing platform adapter sequences and the second end having one or more sequencing platform adapter sequences different from the first end. Having ends with different adapter sequences is useful, e.g., for subsequent solid phase amplification (e.g., cluster generation using the surface-attached P5 and P7 primers in an Illumina®-based sequencing system), DNA sequencing (e.g., using the Read 1 and Read 2 primers in an Illumina®-based sequencing system), and any other steps performed by a sequencing platform requiring different adapter sequences at opposing ends of the nucleic acid to be sequenced.

When the methods include contacting the template nucleic acid with a primer that primes the synthesis of the single product nucleic acid, the primer may include one or more nucleotides (or analogs thereof) that are modified or otherwise non-naturally occurring. For example, the primer may include one or more nucleotide analogs (e.g., LNA, FANA, 2'-O-Me RNA, 2'-fluoro RNA, or the like), linkage modifications (e.g., phosphorothioates, 3'-3' and 5'-5' reversed linkages), 5' and/or 3' end modifications (e.g., 5' and/or 3' amino, biotin, DIG, phosphate, thiol, dyes, quenchers, etc.), one or more fluorescently labeled nucleotides, or any other feature that provides a desired functionality to the primer that primes the synthesis of the single product nucleic acid.

In certain aspects, when the methods include contacting the template nucleic acid with a primer that primes the synthesis of the single product nucleic acid, it may be desirable to prevent any subsequent extension reactions which use the single product nucleic acid as a template from extending beyond a particular position in the region of the single product nucleic acid corresponding to the primer. For example, according to certain embodiments, the primer that primes the synthesis of the single product nucleic acid includes a modification that prevents a polymerase using the region corresponding to the primer as a template from polymerizing a nascent strand beyond the modification. Useful modifications include, but are not limited to, an abasic lesion (e.g., a tetrahydrofuran derivative), a nucleotide adduct, an iso-nucleotide base (e.g., isocytosine, isoguanine, and/or the like), and any combination thereof.

Any nucleic acids that find use in practicing the methods of the present disclosure (e.g., the template switch oligonucleotide, a primer that primes the synthesis of the single product nucleic acid, a second strand synthesis primer, one or more primers for amplifying the product nucleic acid, and/or the like) may include any useful nucleotide analogues and/or modifications, including any of the nucleotide analogues and/or modifications described herein.

As summarized above, the methods of the present disclosure include attaching sequencing platform adapter constructs to ends of the product nucleic acid or a derivative thereof. The adapter constructs attached to the ends of the product nucleic acid or a derivative thereof may include any sequence elements useful in a downstream sequencing application, including any of the elements described above with respect to the optional sequencing platform adapter constructs of the template switch oligonucleotide and/or first strand synthesis primer. For example, the adapter constructs attached to the ends of the product nucleic acid or a derivative thereof may include a nucleic acid domain or complement thereof selected from the group consisting of: a domain that specifically binds to a surface-attached sequencing platform oligonucleotide, a sequencing primer binding domain, a barcode domain, a barcode sequencing primer binding domain, a molecular identification domain, and combinations thereof.

According to certain embodiments, the sequencing platform adapter constructs attached to ends of the product nucleic acid or a derivative thereof are present on a single nucleic acid molecule. In certain aspects, when the sequencing platform adapter constructs are present on a single molecule, attaching the constructs to the product nucleic acid or a derivative thereof produces a circular nucleic acid that includes the product nucleic acid or a derivative thereof and the sequencing platform adapter constructs. Such embodiments find use in a variety of applications, e.g., where it is desirable to join multiple nucleic acid sequence elements on a single nucleic acid. As just one example, when it is desirable to clone the product nucleic acid or a derivative thereof into a vector (e.g., a cloning vector, an expression vector, a viral vector, or any other vector type of interest). As such, when the sequencing platform adapter constructs attached to ends of the product nucleic acid or a derivative thereof are present on a single nucleic acid molecule, the single nucleic acid molecule may further include vector elements of interest, including but not limited to, a selectable marker (e.g., a genetic element that confers on a host organism resistance to a selection agent); a reporter gene (e.g., a gene that encodes a fluorescent protein (e.g., GFP, RFP, or the like), beta-galactosidase, beta-glucuronidase, chloramphenicol acetyltransferase (CAT), or any other useful reporter gene); a promoter (e.g., a T7, T3, or other promoter); an origin of replication (e.g., oriC); a multiple cloning site, or any combination of such elements.

As summarized above, the subject methods include attaching sequencing platform adapter constructs to the ends of the product nucleic acid or a derivative thereof. By "derivative" of the product nucleic acid is meant a modified form of the product nucleic acid and/or a nucleic acid generated from the product nucleic acid. One example of a modified form of the product nucleic acid is a single or double stranded nucleic acid produced by treating the product nucleic acid with an enzyme (e.g., such as a nuclease (e.g., a restriction endonuclease, exonuclease, RNase, or the like), uracil-N-glycosylase (UDG), a uracil-specific excision reagent, and/or the like), a chemical that modifies one or more nucleotides of the product nucleic acid, or any other agent that makes a desired modification to one or more nucleotides of the product nucleic acid.

A derivative which is a nucleic acid generated from the product nucleic acid may be a double stranded nucleic acid produced by second strand synthesis using the single product nucleic acid (i.e., the first strand synthesis product) as a template. For example, in certain aspects, generating a product nucleic acid derivative includes producing the product nucleic acid, contacting a region of the single product nucleic acid complementary to the template switch oligonucleotide with a second-strand synthesis primer configured to bind thereto under hybridization conditions, and synthesizing a second nucleic acid strand from the second strand primer using the single product nucleic acid as a template to generate a double-stranded product nucleic acid derivative. In other aspects, a derivative which is a nucleic acid generated from the product nucleic acid may be an amplicon produced by PCR amplification of the single product nucleic acid as a template. For example, according to certain embodiments, generating a product nucleic acid derivative includes producing the product nucleic acid, and amplifying the single product nucleic acid under PCR amplification conditions to generate a double-stranded product nucleic acid derivative. Any of the primers employed according to the embodiments above, or any primers described elsewhere herein, may include exo-sample nucleotides (described in detail below) when it is desirable, e.g., to generate single-stranded ends from blunt-ended double-stranded extension products.

When the methods of the present disclosure include generating a double-stranded derivative of the product nucleic acid, the methods may include modifying the ends of the double-stranded product nucleic acid derivative to generate a further derivative of the product nucleic acid having single-stranded overhangs at its ends. Sequencing platform adapter constructs may then be attached (e.g., by ligation or other convenient attachment approach) to the product nucleic acid derivative by virtue of having overhangs complementary to the overhangs at the ends of product nucleic acid derivative.

In certain aspects, one or both ends of the double-stranded product nucleic acid or derivative thereof include one or more exo-sample nucleotides to facilitate the generation of overhangs at the ends of the derivative to which sequencing platform adapter constructs having complementary overhangs are attached. By "exo-sample nucleotide" is meant a nucleotide which is generally not found in the type of nucleic acid in which it resides, and which nucleotide marks the site at which it resides for cleavage or degradation. Exo-sample nucleotides of interest include, but are not limited to, deoxyuridine, a ribonucleotide present in a DNA of interest, bromodeoxyuridine, 7-methylguanine, 5,6-dihydroxydeoxythymidine, 3-methyldeoxadenosine, and/or any other useful exo-sample nucleotides. When exo-sample nucleotides are present at one or both ends of the product nucleic acid or derivative thereof, the methods may further include contacting the exo-sample nucleotides with an agent that cleaves the exo-sample nucleotides. For example, the exo-sample nucleotides may be ribonucleotides in an otherwise DNA strand, and the agent that cleaves the ribonucleotides is a ribonuclease (e.g., RNase H). According to certain embodiments, one or both ends of a double-stranded product nucleic acid derivative include deoxyuridine (dU) nucleotides, and the modifying includes contacting the dU nucleotides with uracil-N-glycosylase (UDG), alone or in combination with one or more additional enzymes (e.g., an enzyme having lyase activity, such as the DNA glycosylase-lyase Endonuclease VIII), to generate a derivative of the product nucleic acid having single-stranded ends. UDG cleaves the glycosidic bond between the deoxyribose of the DNA sugar-phosphate backbone and the uracil base, effectively degrading regions of nucleic acids that include dU nucleotides. According to certain embodiments, modifying the ends of the product nucleic acid or a double stranded derivative thereof includes degrading a single strand at each end of the product nucleic acid or a double-stranded derivative thereof using an exonuclease.

In certain aspects, one or both ends of the double-stranded product nucleic acid derivative include a recognition site for a restriction enzyme, and modifying the ends of the double-stranded product nucleic acid derivative includes contacting a restriction enzyme with its recognition site, such that the restriction enzyme cleaves (or "digests") the end. The cleaved end may be a blunt end or a "sticky" end, and attaching the sequencing platform adapter construct may include ligating the construct to the blunt or sticky end. According to certain embodiments, one or more restriction enzyme recognition sites are engineered into the product nucleic acid (e.g., by selection and inclusion of such a recognition site in the template switch oligonucleotide, a first-strand synthesis primer, or both) to facilitate attachment (e.g., ligation) of the sequencing platform adapter constructs to the treated ends of the product nucleic acid or a double-stranded derivative thereof.

Attachment of the sequencing platform adapter constructs may be achieved using any suitable approach. In certain aspects the adapter constructs are attached to the ends of the product nucleic acid or a derivative thereof using an approach that is the same or similar to "seamless" cloning strategies. Seamless strategies eliminate one or more rounds of restriction enzyme analysis and digestion, DNA end-repair, de-phosphorylation, ligation, enzyme inactivation and clean-up, and the corresponding loss of nucleic acid material. Seamless attachment strategies of interest include: the In-Fusion® cloning systems available from Clontech Laboratories, Inc. (Mountain View, Calif.), SLIC (sequence and ligase independent cloning) as described in Li & Elledge (2007) *Nature Methods* 4:251-256; Gibson assembly as described in Gibson et al. (2009) *Nature Methods* 6:343-345; CPEC (circular polymerase extension cloning) as described in Quan & Tian (2009) *PLoS ONE* 4(7): e6441; SLiCE (seamless ligation cloning extract) as described in Zhang et al. (2012) *Nucleic Acids Research* 40(8): e55, and the GeneArt® seamless cloning technology by Life Technologies (Carlsbad, Calif.). According to certain embodiments, the adapter constructs are attached to the ends of the product nucleic acid or a derivative thereof using Gibson assembly, which enables efficient attachment of nucleic acids in a single tube isothermal reaction regardless of fragment length or end compatibility. According to this approach, an exonuclease creates single-stranded 3' overhangs that facilitate the annealing of fragments that share complementarity at one end (overlap region), a polymerase fills in (or "repairs") gaps within each annealed fragment, and a DNA ligase seals nicks in the assembled DNA. The result is a double-stranded fully sealed DNA molecule that can serve as input material for a downstream application of interest, e.g., sequencing using a sequencing platform of interest (with or without amplification prior to sequencing).

A method according to one embodiment of the present disclosure, in which exo-sample nucleotides are present at the ends of a double-stranded product nucleic acid to facilitate the generation of ends having overhangs and attachment of sequencing platform adapter constructs thereto, is schematically illustrated in FIG. 1. As shown, template nucleic acid 102, polymerase 104, template switch oligonucleotide 106, and dNTPs (not shown) are combined into reaction mixture 100 under conditions sufficient to produce the product nucleic acid. The embodiment shown in FIG. 1 employs a first primer, primer 108, which is extended by the polymerase for first strand synthesis. Primer 108 includes first (3') domain 110 that hybridizes to the template nucleic acid and second (5') domain 112 that does not hybridize to the template nucleic acid. The nucleotide sequence of first domain 110 may be arbitrary (e.g., a random sequence, such as a random hexamer sequence) or the sequence of the first domain may be defined (e.g., a sequence specifically selected to hybridize to a particular region of a particular template nucleic acid of interest). In this example, first domain 110 of primer 108 is complementary to sequence 114 within template nucleic acid 102, and second domain 112 includes sequencing platform adapter construct A having one or more sequencing platform nucleic acid domains (e.g., a domain that specifically binds to a surface-attached sequencing platform oligonucleotide, a sequencing primer binding domain, a barcode domain, a barcode sequencing primer binding domain, a molecular identification domain, and combinations thereof). Primer 108 also includes at least one exo-sample nucleotide (indicated by an asterisk FIG. 1).

Upon hybridization of primer 108 to template nucleic acid 102, first strand synthesis proceeds when polymerase 104 extends primer 108 along template nucleic acid 102. In this example, the polymerase has terminal transferase activity, such that when the extension reaction reaches the 5' end of the template nucleic acid, the polymerase adds an arbitrary stretch (e.g., a homo-trinucleotide shown here as XXX) to the extension product. According to this embodiment, template switch oligonucleotide has a 3' hybridization domain that includes a homo-trinucleotide (also shown as XXX) complementary to the arbitrary stretch at the 3' end of the extension product. This complementarity facilitates hybridization of the 3' hybridization domain of the template switch oligonucleotide to the 3' end of the extension product. Hybridization brings the acceptor template region of the template switch oligonucleotide (located 5' of the 3' hybridization domain) within sufficient proximity of the polymerase such that the polymerase can template switch to the acceptor template region and continue the extension reaction to the 5' terminal nucleotide of the template switch oligonucleotide, thereby producing the product nucleic acid that includes the template nucleic acid and the template switch oligonucleotide each hybridized to adjacent regions of the single product nucleic acid.

In this example, the template switch oligonucleotide includes at least one exo-sample nucleotide (indicated by an asterisk FIG. 1), and further includes sequencing platform adapter construct B having one or more sequencing platform nucleic acid domains (e.g., a domain that specifically binds to a surface-attached sequencing platform oligonucleotide, a sequencing primer binding domain, a barcode domain, a barcode sequencing primer binding domain, a molecular identification domain, and combinations thereof), such that the single product nucleic acid includes sequencing platform adapter construct A at its 5' end and sequencing platform adapter construct B at its 3' end. This single product nucleic acid could be used directly for downstream sequencing on a sequencing platform of interest. According to the example embodiment shown in FIG. 1, the method further includes a second strand synthesis step, where the template switch oligonucleotide (or an additional primer complementary to a 3' region of the single product nucleic acid and having one or more deoxyuridine nucleotides) is extended by a polymerase—using the single product nucleic acid as a template—to the 5' end of the single product nucleic acid.

The result of the second strand synthesis step in the embodiment shown in FIG. 1 is a double-stranded product nucleic acid derivative that includes the single product nucleic acid and its complementary strand, which derivative includes a partial sequencing adapter (construct A/A' or construct B/B') and one or more exo-sample nucleotides at each end. The exo-sample nucleotides are contacted with a cleavage agent, to generate a further derivative of the product nucleic acid having single-stranded overhangs at its ends. In this example, sequencing platform adapter construct C is ligated to the end having sequencing adapter construct A' as a single-stranded overhang, and sequencing platform adapter construct D is ligated to the end having sequencing adapter construct B' as a single-stranded overhang. According to this embodiment, the desired directionality of the ligation is facilitated by the presence of "sticky ends," where the A and C overhangs are complementary, and the B and D overhangs are complementary. The ligation produces a nucleic acid corresponding to the template nucleic acid flanked by sequencing platform adapter constructs A and C at one end, and sequencing platform adapter constructs B and D at the other end. Optionally, and as shown in FIG. 1, adapter constructs C and D may be present at the ends of a single nucleic acid molecule, such that ligation of constructs C and D to the cleavage agent-treated ends of the double-stranded product nucleic acid derivative generates a circular nucleic acid.

In the example shown in FIG. 1, adapter constructs A and B do not include all of the sequencing platform nucleic acid domains useful or necessary for downstream sequencing of the nucleotides between the adapters. Rather, the remaining useful or necessary sequencing platform nucleic acid domains (present in adapter constructs C and D) are added via subsequent ligation. One practicing the subject methods may select the sequences of the sequencing platform adapter construct of the first strand synthesis primer, the template switch oligonucleotide, and the sequencing platform adapter constructs to be ligated to the product nucleic acid or derivative thereof, to provide all of the useful or necessary domains in a suitable configuration for sequencing on a sequencing platform of interest. As just one example, constructs A and B may include sequencing primer binding domains (e.g., primer binding domains for the Read 1 and Read 2 sequencing primers employed in Illumina®-based sequencing platforms) or complements thereof, while constructs C and D may include domains that specifically bind to surface-attached sequencing platform oligonucleotides (e.g., domains that specifically bind to the surface-attached P5 and P7 primers of an Illumina® sequencing system) or complements thereof. Any of adapter constructs A-D may include any additional sequence elements useful or necessary for sequencing on a sequencing platform of interest (e.g., barcode sequence elements, barcode sequencing primer binding sequence elements, molecular identification sequence elements, or any other desirable sequence element). Optionally, the nucleic acid corresponding to the template nucleic acid and flanking sequencing platform adapter constructs may be amplified to generate a greater amount of starting material for the sequencing application (e.g., if the amount of starting material in the absence of amplification is insufficient/sub-optimal for the sequencing platform of interest).

Any suitable approach may be employed for providing additional nucleic acid sequencing domains to a product nucleic acid or derivative thereof having less than all of the useful or necessary sequencing domains for a sequencing platform of interest. For example, the product nucleic acid or derivative thereof could be amplified using PCR primers having adapter sequences at their 5' ends (e.g., 5' of the region of the primers complementary to the product nucleic acid or derivative thereof), such that the amplicons include the adapter sequences in the original product nucleic acid as well as the adapter sequences in the primers, in any desired configuration. Other approaches, including those based on seamless cloning strategies, restriction digestion/ligation, or the like may be employed.

In certain aspects, the product nucleic acid or derivative thereof does not include any nucleic acid sequencing domains, such that all of the sequencing domains useful or necessary for downstream sequencing on a sequencing platform of interest are provided by the sequencing platform adapter constructs attached to the ends of the product nucleic acid or a derivative thereof. Such attachment may be performed using any of the approaches described herein.

Figure 2:
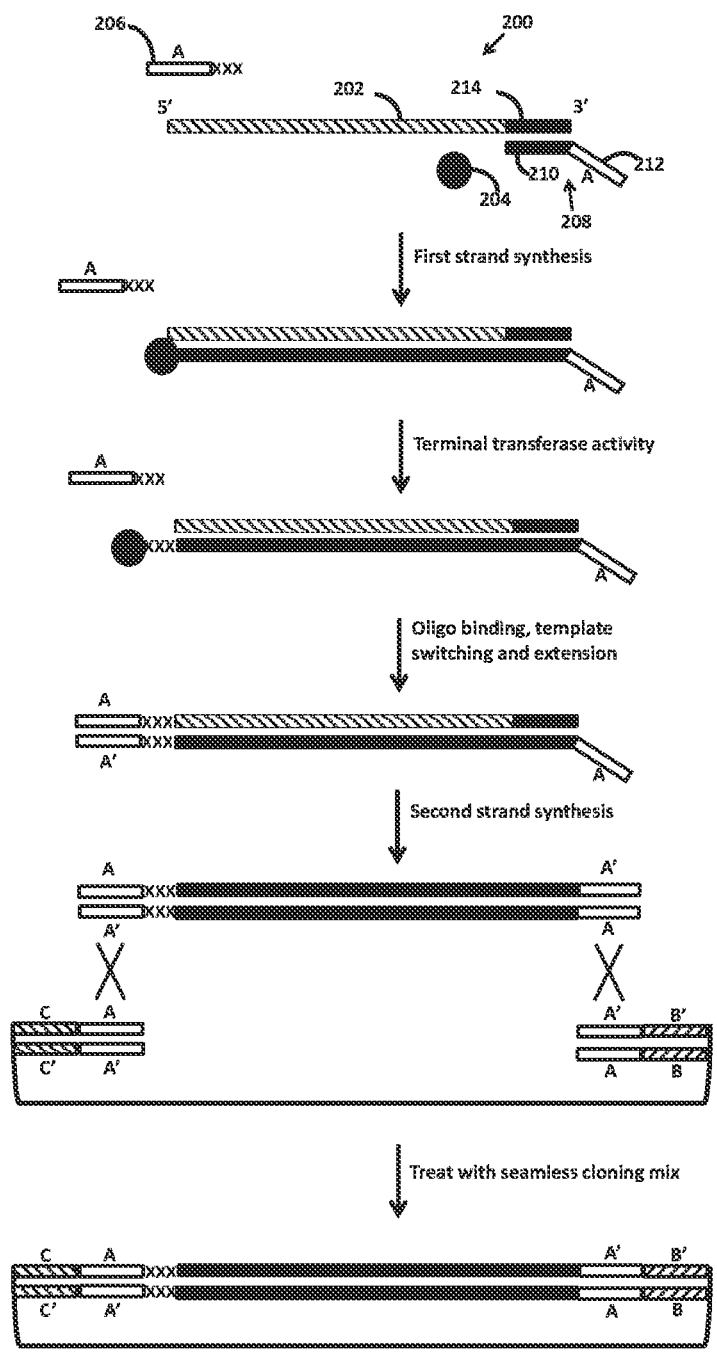
FIG. 2 schematically illustrates a template switch-based method for generating a nucleic acid having adapter constructs according to one embodiment of the present disclosure. In this embodiment, following first and second strand synthesis reactions, sequencing platform adapter constructs are attached to the ends of the product nucleic acid derivative using seamless cloning conditions.

A method according to another embodiment of the present disclosure is schematically illustrated in FIG. 2. First strand synthesis that utilizes template switching is carried out similar to the first strand synthesis shown in FIG. 1. According to this embodiment, however, at least a region of the first strand synthesis primer is the same or substantially the same as a region of the template switch oligonucleotide, and a double-stranded product nucleic acid derivative is generated using single primer suppression PCR (e.g., to suppress amplification of short sequences, such as primer dimers and/or artifacts generated during the first-strand synthesis reaction).

According to the embodiment shown in FIG. 2, after suppression PCR, sequencing platform adapter constructs are attached to the ends of the amplicons by treatment with a seamless cloning mix, such as a mixture of reagents suitable for Gibson assembly as described hereinabove. As is true for any of the embodiments described herein, the sequencing platform adapter constructs may be on separate nucleic acid molecules, or may be present on a single nucleic acid molecule. In the particular embodiment shown in FIG. 2, the constructs are present at the ends of a single nucleic acid molecule such that upon attachment of the adapter constructs to the product nucleic acid or a derivative thereof, a circular nucleic acid species (e.g., a cloning vector, or any other circular nucleic acid species of interest) is generated that includes a nucleic acid corresponding to the template nucleic acid flanked by at least one sequencing platform adapter construct on each end.

Figure 3:
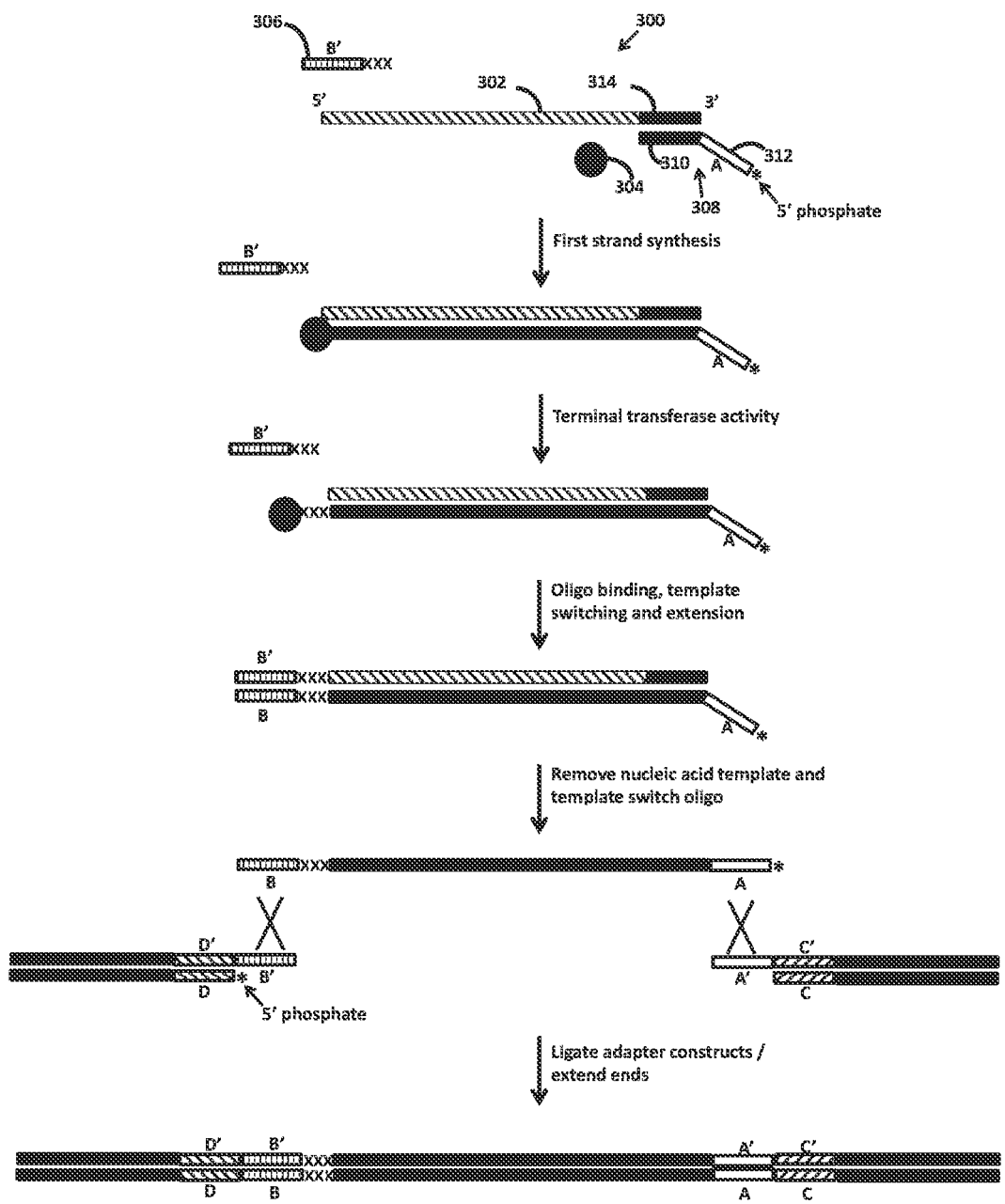
FIG. 3 schematically illustrates a template switch-based method for generating a nucleic acid having adapter constructs according to one embodiment of the present disclosure. In this embodiment, the template nucleic acid and template switch oligonucleotide are removed following first strand synthesis. Sequencing platform adapter constructs are then attached by ligation to the single product nucleic acid.

In certain aspects, generating a product nucleic acid derivative includes producing the product nucleic acid, and degrading the template nucleic acid and the template switch oligonucleotide to generate a single-stranded product nucleic acid derivative. An example method according to this embodiment is schematically illustrated in FIG. 3. In this example, first strand synthesis that utilizes template switching is carried out in a manner similar to the first strand syntheses shown in FIGS. 1 and 2. The primer(s) used for the initial reaction (e.g., the first strand synthesis primer) either has a 5' phosphate (indicated by asterisks in FIG. 3), or else is treated with polynucleotide kinase to provide the 5' phosphate(s). The product nucleic acid (which in this example includes a template RNA) is then treated with a nuclease to remove the template nucleic acid, and optionally, the template switch oligonucleotide. For example, when the template nucleic acid is a template RNA, the removal may be effected using a ribonuclease (e.g., RNase H). The template switch oligonucleotide may also be removed using the same or a separate approach, such as providing a template switch oligonucleotide having exo-sample nucleotides and contacting the exo-sample nucleotides with a cleavage agent (e.g., UDG when the exo-sample nucleotides are dU, RNase H when the exo-sample nucleotides are ribonucleotides, etc.). In this example, the single product nucleic acid has a sequencing platform adapter construct at each end, where the adapter construct at the 5' end is different from the adapter construct at the 3' end. As such, attaching sequencing platform adapter constructs to the ends of the single product nucleic acid may be achieved in a directional manner. As shown, the sequencing platform adapter constructs to be attached to the ends of the single product nucleic acid have single-stranded overhangs that facilitate attachment (e.g., annealing and/or ligation) of the overhangs to the ends of the single product nucleic acid. Upon attachment of the sequencing platform adapter constructs to the ends of the single product nucleic acid, a nucleic acid species is generated that includes a nucleic acid corresponding to the template nucleic acid flanked by all of the desirable or necessary sequencing adapters for sequencing on a sequencing platform of interest.

Figure 4:
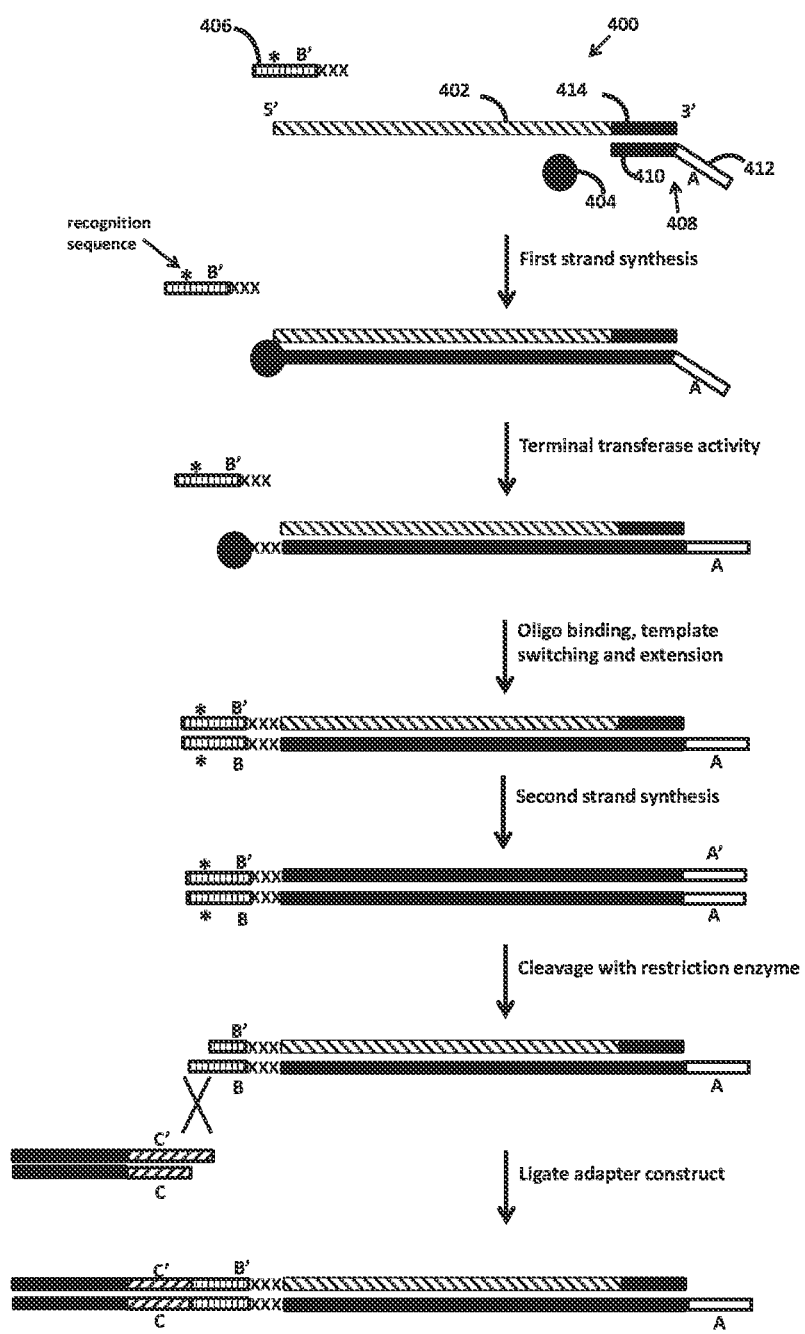
FIG. 4 schematically illustrates a template switch-based method for generating a nucleic acid having adapter constructs according to one embodiment of the present disclosure. In this embodiment, the template switch oligonucleotide includes a restriction enzyme recognition sequence. Following first and second strand synthesis, a suitable restriction enzyme cleaves the recognition sequence, thereby creating an end compatible for ligation to a sequencing platform adapter construct.

According to certain embodiments, generating a product nucleic acid derivative includes producing the product nucleic acid, and digesting the product nucleic acid using a restriction enzyme. In certain aspects, the digesting is in a duplex region formed by the single product nucleic acid and the template switch oligonucleotide. An example method according to this embodiment is schematically illustrated in FIG. 4. First strand synthesis that utilizes template switching is carried out in a manner similar to the first strand syntheses shown in the embodiments of FIGS. 1-3. In this example, the template switch oligonucleotide includes a restriction enzyme recognition sequence (indicated by an asterisk in FIG. 4). The recognition sequence may be for a restriction enzyme that leaves a sticky end upon cleaving the recognition sequence. Alternatively, the recognition sequence may be for a restriction enzyme that leaves a blunt end upon cleaving the recognition sequence. The product nucleic acid produced by the first strand reaction is treated with the restriction enzyme, which only cuts the product nucleic acid in the duplex region formed by the single product nucleic acid and the template switch oligonucleotide. A sequencing platform adapter construct is then ligated to the digested end of the duplex region between the single product nucleic acid and the template switch oligonucleotide. As shown in the example embodiment of FIG. 4, the digested end may include a sticky end (i.e., a 3' overhang) complementary to a sticky end of the sequencing platform adapter construct to facilitate attachment of the adapter construct to the digested end of the product nucleic acid.

Once the product nucleic acid or a derivative thereof is produced, and after the sequencing platform adapter constructs have been attached to the ends of the product nucleic acid or a derivative thereof, the methods may include inputting the product nucleic acid or derivative thereof with adapter constructs directly into a downstream application of interest (e.g., a sequencing application, etc.). In other aspects, the methods may include using the product nucleic acid or derivative thereof with adapter constructs as a template for PCR amplification (e.g., for subsequent sequencing of the amplicons). According to one embodiment, the methods of the present disclosure further include subjecting the product nucleic acid or derivative thereof with adapter constructs to nucleic acid amplification conditions. Such conditions may include the addition of forward and reverse primers configured to amplify all or a desired portion of the product nucleic acid, dNTPs, and a polymerase suitable for effecting the amplification (e.g., a thermostable polymerase). The single product nucleic acid may have an amplification sequence at its 5' end and an amplification sequence at its 3' end, and be subjected to PCR amplification conditions with primers complementary to the 5' and 3' amplification sequences. The amplification sequences may be (or overlap with) a nucleic acid domain in a sequencing platform adapter construct, or may be outside of a sequencing platform adapter construct. An initial step in carrying out the amplification may include denaturing the product nucleic acid or derivative thereof with adapter constructs to dissociate any double stranded regions, thereby making the single strands available for primer binding.

In certain aspects, when the product nucleic acid or derivative thereof with adapter constructs is amplified following its production, the amplification may be carried out using a primer pair in which one or both of the primers include one or more additional sequencing platform adapter constructs. The sequencing platform adapter construct(s) present in the amplification primers may include any of the nucleic acid domains described elsewhere herein (e.g., a domain that specifically binds to a surface-attached sequencing platform oligonucleotide, a sequencing primer binding domain, a barcode domain, a barcode sequencing primer binding domain, a molecular identification domain, or any combination thereof). Such embodiments finds use, e.g., where the product nucleic acid or derivative thereof with adapter constructs does not include all of the adapter domains useful or necessary for sequencing in a sequencing platform of interest, and the remaining adapter domains are provided by the primers used for the amplification of the product nucleic acid or derivative thereof with adapter constructs.

In certain embodiments, the subject methods may be used to generate a library of nucleic acids of interest (e.g., a cDNA library, a library corresponding to genomic DNA fragments, or a library corresponding to any other nucleic acids of interest) for downstream sequencing on a sequencing platform of interest (e.g., a sequencing platform provided by Illumina®, Ion Torrent™, Pacific Biosciences, Life Technologies™, Roche, or the like). For example, first strand synthesis primers designed to amplify a plurality of different nucleic acids in a nucleic acid sample of interest may be employed, such that product nucleic acids corresponding to the plurality of different nucleic acids are generated. Sequencing platform adapter constructs may then be attached to the ends of these product nucleic acids or derivatives thereof, according to any of the strategies described hereinabove. After attachment of the adapter constructs, these nucleic acid species may be inputted directly for sequencing on a sequencing platform of interest, or alternatively, amplicons generated upon PCR amplification of these nucleic acid species may serve as the input for the sequencing application of interest. According to certain embodiments, the subject methods are used to generate a cDNA library corresponding to polyadenylated or non-polyadenylated RNAs for downstream sequencing on an Illumina®-based sequencing system. In one embodiment, microRNAs are polyadenylated (as described hereinabove) and then used as templates in a template switch polymerization reaction as described elsewhere herein to produce product nucleic acids for adapter construct attachment and subsequent sequencing. In such embodiments, the number of distinct nucleic acids of differing sequence in the library may vary, and in some instances may range from 2 to 100,000 (e.g., from 30,000 to 100,000), such as from 50 to 25,000, from 100 to 10,000, or from 150 to 5,000, e.g., from 200 to 1000.

The subject methods may further include combining a thermostable polymerase (e.g., a Taq, Pfu, Tfl, Tth, Tli, and/or other thermostable polymerase)—in addition to the template switching polymerase—into the reaction mixture. Alternatively, the template switching polymerase may be a thermostable polymerase. Either of these embodiments find use, e.g., when it is desirable to achieve first strand synthesis and amplification (e.g., amplification with or without sequencing adapter construct addition) of the product nucleic acid in a single tube. For example, the contents of the single tube may be placed under conditions suitable for the template switch polymerization reaction to occur (as described elsewhere herein), followed by placing the reaction contents under thermocycling conditions (e.g., denaturation, primer annealing, and polymerization conditions) in which the first-strand synthesis product is PCR amplified using amplification primers and the thermostable polymerase present in the single tube. Due to its thermostability, the thermostable polymerase will retain its activity even when present during the first-strand synthesis phase of this embodiment.

Compositions

Also provided by the present disclosure are compositions. The subject compositions may include, e.g., one or more of any of the reaction mixture components described above with respect to the subject methods. For example, the compositions may include one or more of a template nucleic acid (e.g., a template DNA or a template RNA), a polymerase (e.g., a polymerase capable of template-switching, a thermostable polymerase, combinations thereof, or the like), a template switch oligonucleotide, one or more sequencing platform adapter constructs, dNTPs, a salt, a metal cofactor, one or more nuclease inhibitors (e.g., an RNase inhibitor), one or more enzyme-stabilizing components (e.g., DTT), or any other desired reaction mixture component(s).

In certain aspects, the subject compositions include a template nucleic acid (e.g., a template DNA or a template RNA), a template switch oligonucleotide, and a sequencing platform adapter construct, where the template nucleic acid and template switch oligonucleotide are each hybridized to adjacent regions of a nucleic acid strand. The sequencing platform adapter construct may include any sequencing platform nucleic acid domain of interest, including any of the domains described above with respect to the subject methods (e.g., a domain that specifically binds to a surface-attached sequencing platform oligonucleotide, a sequencing primer binding domain, a barcode domain, a barcode sequencing primer binding domain, a molecular identification domain, or any combination thereof). Approaches for isolating DNA or RNA samples from a nucleic acid source of interest, as well as strategies for generating template DNAs or RNAs from precursor DNAs or RNAs, are described elsewhere herein.

In certain aspects, the template switch oligonucleotide includes a 3' hybridization domain. According to certain embodiments, the 3' hybridization domain of the template switch oligonucleotide includes an arbitrary stretch (e.g., a homo-trinucleotide or hetero-trinucleotide).

The subject compositions may be present in any suitable environment. According to one embodiment, the composition is present in a reaction tube (e.g., a 0.2 mL tube, a 0.6 mL tube, a 1.5 mL tube, or the like) or a well. In certain aspects, the composition is present in two or more (e.g., a plurality of) reaction tubes or wells (e.g., a plate, such as a 96-well plate). The tubes and/or plates may be made of any suitable material, e.g., polypropylene, or the like. In certain aspects, the tubes and/or plates in which the composition is present provide for efficient heat transfer to the composition (e.g., when placed in a heat block, water bath, thermocycler, and/or the like), so that the temperature of the composition may be altered within a short period of time, e.g., as necessary for a particular enzymatic reaction to occur. According to certain embodiments, the composition is present in a thin-walled polypropylene tube, or a plate having thin-walled polypropylene wells.

Other suitable environments for the subject compositions include, e.g., a microfluidic chip (e.g., a "lab-on-a-chip device"). The composition may be present in an instrument configured to bring the composition to a desired temperature, e.g., a temperature-controlled water bath, heat block, or the like. The instrument configured to bring the composition to a desired temperature may be configured to bring the composition to a series of different desired temperatures, each for a suitable period of time (e.g., the instrument may be a thermocycler).

Kits

Aspects of the present disclosure also include kits. The kits may include, e.g., one or more of any of the reaction mixture components described above with respect to the subject methods. For example, the kits may include one or more of a template DNA or template RNA, components for producing a template DNA or RNA from a precursor DNA or RNA (e.g., a poly(A) polymerase and associated reagents for polyadenylating a non-polyadenylated precursor RNA), a polymerase (e.g., a polymerase capable of template-switching, a thermostable polymerase, combinations thereof, or the like), a template switch oligonucleotide, dNTPs, a salt, a metal cofactor, one or more nuclease inhibitors (e.g., an RNase inhibitor and/or a DNase inhibitor), one or more molecular crowding agents (e.g., polyethylene glycol, or the like), one or more enzyme-stabilizing components (e.g., DTT), or any other desired kit component(s).

According to one embodiment, the subject kits include a template switch oligonucleotide, a sequencing platform adapter construct, and a template switching polymerase. The sequencing platform adapter construct may include any sequencing platform nucleic acid domain of interest, including any of the domains described above with respect to the subject methods and compositions (e.g., a domain that specifically binds to a surface-attached sequencing platform oligonucleotide, a sequencing primer binding domain, a barcode domain, a barcode sequencing primer binding domain, a molecular identification domain, a complement of any such domains, or any combination thereof). In certain aspects, the template switching polymerase is a reverse transcriptase.

Kits of the present disclosure may include a first-strand synthesis primer that includes a first domain that hybridizes to a template nucleic acid and a second domain that does not hybridize to the template nucleic acid. The first domain may have a defined or arbitrary sequence. The second domain of such primers may include, e.g., a sequencing platform adapter construct that includes a nucleic acid domain selected from a domain that specifically binds to a surface-attached sequencing platform oligonucleotide, a sequencing primer binding domain, a barcode domain, a barcode sequencing primer binding domain, a molecular identification domain, a complement of any such domains, and any combination thereof.

In certain embodiments, the kits include reagents for isolating DNA or RNA from a nucleic acid source of interest. The reagents may be suitable for isolating nucleic acid samples from a variety of DNA or RNA sources including single cells, cultured cells, tissues, organs, or organisms. The subject kits may include reagents for isolating a nucleic acid sample from a fixed cell, tissue or organ, e.g., formalin-fixed, paraffin-embedded (FFPE) tissue. Such kits may include one or more deparaffinization agents, one or more agents suitable to de-crosslink nucleic acids, and/or the like.

Components of the kits may be present in separate containers, or multiple components may be present in a single container. For example, the template switch oligonucleotide, the sequencing platform adapter construct, and the template switching polymerase may be provided in the same tube, or may be provided in different tubes.

In addition to the above-mentioned components, a subject kit may further include instructions for using the components of the kit, e.g., to practice the subject methods. The instructions are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging) etc. In other embodiments, the instructions are present as an electronic storage data file present on a suitable computer readable storage medium, e.g. CD-ROM, diskette, Hard Disk Drive (HDD) etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate.

Utility

The subject methods find use in a variety of applications, including those that require the presence of particular nucleotide sequences at one or both ends of nucleic acids of interest. Such applications exist in the areas of basic research and diagnostics (e.g., clinical diagnostics) and include, but are not limited to, the generation of sequencing-ready libraries of nucleic acids of interest, suppression PCR, cloning, detection, library amplification, array hybridization, whole genome amplification, and/or the like. The sequencing-ready libraries include adapter sequences that enable sequencing of the library members using any convenient sequencing platform, including: the HiSeq™, MiSeq™ and Genome Analyzer™ sequencing systems from Illumina®; the Ion PGM™ and Ion Proton™ sequencing systems from Ion Torrent™; the PACBIO RS II sequencing system from Pacific Biosciences, the SOLiD sequencing systems from Life Technologies™, the 454 GS FLX+ and GS Junior sequencing systems from Roche, or any other convenient sequencing platform. The methods of the present disclosure find use in generating sequencing ready libraries corresponding to any DNA or RNA starting material of interest, e.g., genomic DNA, mRNA, non-polyadenylated RNA (e.g., microRNA). For example, the subject methods may be used to generate sequencing-ready cDNA libraries from non-polyadenylated RNAs, including microRNAs, small RNAs, siRNAs, and/or any other type non-polyadenylated RNAs of interest.

In certain sequencing applications, the cumulative length of the required sequencing adapters is great enough that providing the required adapters in a single template-switching reaction is inefficient or not possible. An aspect of the subject methods is that they permit the ready provision of any required sequencing adapters to nucleic acids of interest, where such sequencing adapters might otherwise exceed the length permitted using approaches involving a single template-switching reaction.

The following example is offered by way of illustration and not by way of limitation.

EXPERIMENTAL

Double-stranded cDNA was generated using a SMARTer® Universal cDNA synthesis kit (Clontech Laboratories, Mountain View, Calif.) by single-primer amplification with the IIA sequence on both ends. cDNA (0.06 pmol (approx. 10 ng)) was combined with 0.06 pmol linker PCR product having 30 by or 15 by of the 5' and '3 end complementary to the IIA primer sequence, flanking the Illumina P5 and P7 sequences. Samples were treated with Gibson Assembly® mix (New England Biolabs) for 1 hr at 50° C., and then purified using a Gel and PCR Clean-up kit (Machery-Nagel). Samples were then subjected to 12 cycles of PCR using P5 and P7 PCR primers. The resulting PCR product was run on a high sensitivity chip in an Agilent Bioanalyzer. Amplification was only seen when the SMARTer product was present, and not in negative controls. The cDNA distribution was similar to the input.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A method comprising:
   (a) combining:
      a template nucleic acid;
      a template switch oligonucleotide comprising a 3' hybridization domain and one or more ribonucleotides 5' of the 3' hybridization domain;
      a polymerase; and
      dNTPs;
   in a reaction mixture under conditions sufficient to produce a first strand cDNA complementary to the template nucleic acid and the template switch oligonucleotide;
   b) degrading the template switch oligonucleotide; and
   c) amplifying the first strand cDNA.

2. The method according to claim 1, wherein the template switch oligonucleotide comprises two or more ribonucleotides 5' of the 3' hybridization domain.

3. The method according to claim 1, wherein the template switch oligonucleotide is degraded using a ribonuclease.

4. The method according to claim 1, wherein the amplifying is performed with a primer comprising a barcode.

5. The method according to claim 1, wherein said template nucleic acid is from a single cell.

6. The method according to claim 1, wherein the 3' hybridization domain comprises a homo-trinucleotide.

7. The method according to claim 1, wherein the 3' hybridization domain comprises a hetero-trinucleotide.

8. The method according to claim 1, wherein the template switch oligonucleotide comprises a sequencing platform nucleic acid domain selected from the group consisting of: a domain that specifically binds to a surface-attached sequencing platform oligonucleotide, a sequencing primer binding domain, a barcode domain, a barcode sequencing primer binding domain, a molecular identification domain, a complement of any such domains, and combinations thereof.

9. The method according to claim 1, wherein the template nucleic acid is sheared or fragmented template nucleic acid.

10. The method according to claim 9, wherein the method further comprises shearing or fragmenting the template nucleic acid prior to the combining.

11. The method according to claim 1, wherein the method comprises heating the reaction mixture.

12. The method according to claim 1, wherein the reaction mixture includes a first strand synthesis primer comprising at least one exo-sample nucleotide.

13. The method according to claim 1, wherein the degrading comprises degrading dissociated template switch oligonucleotide.

14. A method comprising:
   (a) combining:
      a template nucleic acid;
      a template switch oligonucleotide comprising one or more exo-sample nucleotides selected from the group consisting of: bromodeoxyuridine, 7-methylguanine, 5,6-dihydroxydeoxythymidine, and 3-methyldeoxadenosine, or any combination thereof and a 3' hybridization domain;
      a polymerase; and
      dNTPs;
   in a reaction mixture under conditions sufficient to produce a first strand cDNA complementary to the template nucleic acid and the template switch oligonucleotide;
   b) degrading a portion of the template switch oligonucleotide that is 5' of the 3' hybridization domain; and
   c) amplifying the first strand cDNA.

15. The method according to claim 14, wherein template switch oligonucleotide is degraded using one or more enzymes.

16. The method according to claim 15, wherein the one or more enzymes are selected from the group consisting of: a uracil-N-glycosylase, a lyase, a DNA glycosylase-lyase and combinations thereof.

17. The method according to claim 16, wherein the DNA glycosylase-lyase is Endonuclease VIII.

18. The method according to claim 14, wherein the template switch oligonucleotide further comprises a ribonucleotide 5' of the 3' hybridization domain.

19. The method according to claim 14, wherein the template switch oligonucleotide comprises a sequencing platform nucleic acid domain selected from the group consisting of: a domain that specifically binds to a surface-attached sequencing platform oligonucleotide, a sequencing primer binding domain, a barcode domain, a barcode sequencing primer binding domain, a molecular identification domain, a complement of any such domains, and combinations thereof.

* * * * *

SEQUENCE LISTING

<160> NUMBER OF SEQ ID NOS: 6

<210> SEQ ID NO 1
<211> LENGTH: 24
<212> TYPE: DNA
<213> ORGANISM: Artificial Sequence
<220> FEATURE:
<223> OTHER INFORMATION: synthetic polynucleotide

<400> SEQUENCE: 1
caagcagaag acggcatacg agat                                              24

<210> SEQ ID NO 2
<211> LENGTH: 33
<212> TYPE: DNA
<213> ORGANISM: Artificial Sequence
<220> FEATURE:
<223> OTHER INFORMATION: synthetic polynucleotide

<400> SEQUENCE: 2
acactctttc cctacacgac gctcttccga tct                                    33

<210> SEQ ID NO 3
<211> LENGTH: 34
<212> TYPE: DNA
<213> ORGANISM: Artificial Sequence
<220> FEATURE:
<223> OTHER INFORMATION: synthetic polynucleotide

<400> SEQUENCE: 3
gtgactggag ttcagacgtg tgctcttccg atct                                   34

```
<210> SEQ ID NO 4
<211> LENGTH: 30
<212> TYPE: DNA
<213> ORGANISM: Artificial Sequence
<220> FEATURE:
<223> OTHER INFORMATION: synthetic polynucleotide

<400> SEQUENCE: 4
ccatctcatc cctgcgtgtc tccgactcag                                       30

<210> SEQ ID NO 5
<211> LENGTH: 23
<212> TYPE: DNA
<213> ORGANISM: Artificial Sequence
<220> FEATURE:
<223> OTHER INFORMATION: synthetic polynucleotide

<400> SEQUENCE: 5
cctctctatg ggcagtcggt gat                                              23

<210> SEQ ID NO 6
<211> LENGTH: 20
<212> TYPE: DNA
<213> ORGANISM: Artificial Sequence
<220> FEATURE:
<223> OTHER INFORMATION: synthetic polynucleotide

<400> SEQUENCE: 6
aatgatacgg cgaccaccga                                                  20
```